(12) United States Patent
Blum et al.

(10) Patent No.: US 10,220,118 B2
(45) Date of Patent: Mar. 5, 2019

(54) SELF-REPLENISHING BOUNDARY LUBRICATION IN HYDROGELS USING ZWITTERIONIC POLYMERS

(71) Applicants: Michelle M. Blum, Jamesville, NY (US); Patrick T. Mather, Oxford, PA (US); Allen Osaheni, Clifton Park, NY (US)

(72) Inventors: Michelle M. Blum, Jamesville, NY (US); Patrick T. Mather, Oxford, PA (US); Allen Osaheni, Clifton Park, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 0 days.

(21) Appl. No.: 15/335,361

(22) Filed: Oct. 26, 2016

(65) Prior Publication Data
US 2017/0112970 A1    Apr. 27, 2017

Related U.S. Application Data

(60) Provisional application No. 62/246,327, filed on Oct. 26, 2015.

(51) Int. Cl.

| | |
|---|---|
| *A61L 27/52* | (2006.01) |
| *A61L 27/26* | (2006.01) |
| *A61L 27/50* | (2006.01) |
| *A61L 27/48* | (2006.01) |
| *A61L 31/14* | (2006.01) |
| *A61L 31/10* | (2006.01) |
| *A61L 29/08* | (2006.01) |
| *A61L 29/14* | (2006.01) |

(52) U.S. Cl.
CPC ............... *A61L 27/52* (2013.01); *A61L 27/26* (2013.01); *A61L 27/48* (2013.01); *A61L 27/50* (2013.01); *A61L 29/085* (2013.01); *A61L 29/14* (2013.01); *A61L 29/145* (2013.01); *A61L 31/10* (2013.01); *A61L 31/14* (2013.01); *A61L 31/145* (2013.01); *A61L 2400/10* (2013.01); *A61L 2430/06* (2013.01)

(58) Field of Classification Search
CPC ...................................................... A61L 27/52
See application file for complete search history.

(56) References Cited

U.S. PATENT DOCUMENTS

| | | | | |
|---|---|---|---|---|
| 9,006,359 | B2 * | 4/2015 | Zhang ............ | C08G 77/388 525/479 |
| 2003/0232895 | A1 * | 12/2003 | Omidian .......... | A61K 9/0065 521/99 |
| 2005/0228120 | A1 * | 10/2005 | Hughes ............ | A61F 2/14 524/588 |
| 2011/0245400 | A1 * | 10/2011 | Wear ............... | C08F 2/18 524/458 |

* cited by examiner

*Primary Examiner* — Kyle A Purdy
(74) *Attorney, Agent, or Firm* — Bond Schoeneck and King PLLC; David Nocilly; George McGuire

(57) ABSTRACT

A self-replenishing biocompatible hydrogel having a zwitterionic polymer embedded throughout the matrix system to act as a lubricant and a surface modified with the same zwitterionic polymer. When surface material loss occurs in the hydrogel, such as a surface crack or a scratch, the damage propagates through the matrix rupturing the pockets of lubricant. The zwitterionic polymer is then drawn into the site due to the change in entropy at the surface and the positive and negative charge groups of the side chains fuse across the damage cite due to strong electrostatic attraction causing inter-chain association.

16 Claims, 28 Drawing Sheets

SELF-REPLENISHING BOUNDARY LUBRICATION IN HYDROGELS USING ZWITTERIONIC POLYMERS

CROSS-REFERENCE TO RELATED APPLICATIONS

The present application claims priority to U.S. Provisional App. No. 62/246,327, filed on Oct. 26, 2016.

BACKGROUND OF THE INVENTION

1. Field of the Invention

The present invention relates to hydrogels and, more particularly, to a hydrogel having zwitterionic polymers for lubrication.

2. Description of the Related Art

Innovative technology strives to create advanced materials who properties delay the degradation and extend performance. One such material are a class of biphasic synthetic polymer materials that swell in the presence of liquids, yet are insoluble due to their cross-linked structure, called hydrogels. Hydrogels function in a wide variety of biomaterials applications; including stent coatings, prophylactic protection devices, artificial tissue implants, and tissue engineering scaffolds. Thus far, the design of hydrogel systems has emphasized replication of structural and mechanical properties, but in order for these types of materials to reach their full potential as biomaterials it is imperative that hydrogel materials possess improved tribological and lubrication properties, because the major limitation of synthetic hydrogels is that they do not possess exceptional surface and friction properties. Poor surface and boundary lubrication makes hydrogels incompatible with other natural surfaces, leading the constructs to wear, fail, and damage contacting natural tissue. Thus, there is a need in the art for a hydrogel having improved tribological and lubrication properties.

BRIEF SUMMARY OF THE INVENTION

The present invention comprises new process strategies for creating hydrogels with self-replenishing improved surface-friction and wear properties and exemplary hydrogels made according to the strategies. More particularly, the present invention provides for self-replenishing lubrication of hydrogels by taking advantage of strong affinity of the constituent zwitterionic polymers for water and their freedom to diffuse to the surface, thereby forming a new class of hydrogel technologies.

In one embodiment, the invention comprise a hydrogel having self-replenishing lubrication formed from a matrix formed from a hydrogel polymer and a plurality of zwitterionic polymer molecules embedded in the matrix. The hydrogel polymer comprises poly(vinyl alcohol) and the zwitterionic polymer molecules comprise poly[2-(Methacryloyloxy) ethyl]dimethyl-(3-sulfopropyl) ammonium hydroxide). The hydrogel polymer may also comprises poly(vinyl alcohol) and an initiator grafted to a surface of the poly(vinyl alcohol). The initiator may be α-chlorophenylacetyl chloride or α-bromoisobutyryl bromide, and the plurality of zwitterionic polymer molecules are polymerized from the bromide initiator. The resulting hydrogel has an average modulus of above one Megapascal.

In another embodiment, the invention comprises a method of making a hydrogel having self-replenishing lubrication by forming a plurality of zwitterionic polymer molecules, blending the plurality of zwitterionic polymer molecules with a hydrogel polymer, and subjecting the blended zwitterionic polymer molecules and polymer to a predetermined number of freeze-thaw cycles to embed the zwitterionic polymer molecules in a matrix of the hydrogel polymer.

In a further embodiment, the invention comprises a method of making a hydrogel having self-replenishing lubrication by grafting an initiator to a surface of a dry hydrogel polymer and initiating polymerization of plurality of zwitterionic molecules from the initiator of the surface of the dry hydrogel polymer. The step of grafting the initiator to the surface of the dry hydrogel is performed in the presence of tetrahydrofuran. The step of initiating polymerization of plurality of zwitterionic molecules from the initiator of the surface of the dry hydrogen polymer is performed in the presence of triflureoethanol.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIGS. 1(a) through 1(c) is a schematic of self-replenishing lubrication according to the present invention;

FIG. 2 is a schematic of zwitterionic polymer and hydrogel blend according to the present invention;

FIGS. 3(a) through 3(e) is a schematic of the fabrication of polyvinyl alcohol and poly[2-(methacryloyloxy) ethyl] dimethyl-(3-sulfopropyl) ammonium hydroxide (PVA-poly (MEDSAH)) blends, showing: (a) the chemical structure of PVA; (b) the chemical structure of poly(MEDSAH); (c) the solvent casting process; (d) the freeze thaw process; and (e) the viable structure of PVA-poly(MEDSAH) blend following solvent exchange;

DETAILED DESCRIPTION OF THE INVENTION

Figure 1A:
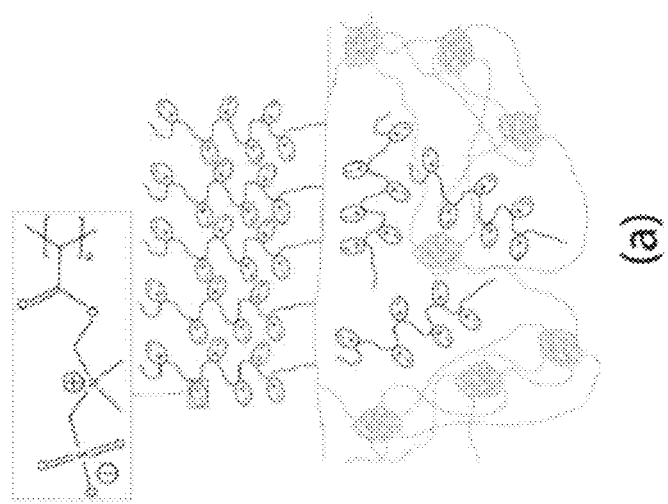
Figure 1B:
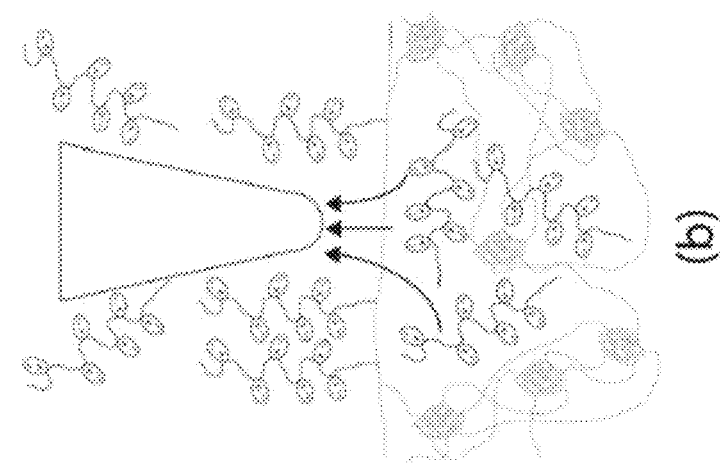
Figure 1C:
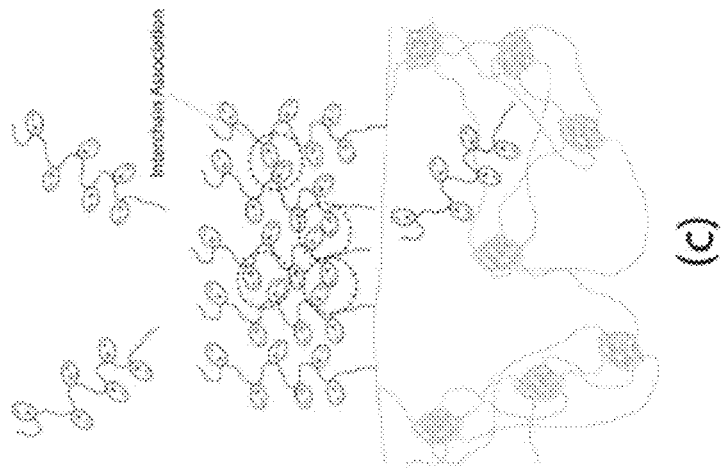

Referring now to the drawings, wherein like reference numerals refer to like parts throughout, there is seen in FIG. 1($a$) through 1($c$) a schematic of a hydrogel having self-replenishing lubrication via zwitterionic polymer molecules that blended throughout the hydrogel polymer matrix. When surface material loss occurs in the hydrogel, such as a surface crack or a scratch, the damage propagates through the matrix engaging the reservoir of lubricant, as seen in FIG. 1($b$). The zwitterionic polymer is then drawn into the site of surface material loss due to the change in entropy at the surface and the positive and negative charge groups of the side chains of the zwitterionic polymer fuse across the damage cite due to strong electrostatic attraction that causes inter-chain association, as seen in FIG. 1($c$). The result is that the boundary lubricant surface layer is repaired. Alternatively, self-replenishing may be achieved through the incorporation of a vascular system as an internal reservoir rather than pockets.

During wear to the surface, the interaction of mechanical and chemical kinetics governs the efficiency of self-replenishing lubrication and whether any prevention of wear rate or extension of life is achieved. For example, if mechanical kinetics dominates, namely abrasive or fretting wear, then surface damage is relatively fast and any chemistry that is triggered along the damage site is not allowed to reach completion. The damaged surface essentially experiences no influence of self-replenishing functionality. Alternatively, if chemical kinetics dominates, which can occur during adhesive or fatigue wear, the wear rate is relatively slow and the chemistry that is triggered by the damage reaches sufficient completion before the damage propagates. In this case, the functionality of self-replenishing boundary lubrication is achieved and wear rates can be reduced and perhaps fully arrested.

The present invention surprisingly provides for a system with great mechanical stiffness and strength. While conventional hydrogels have elastic modulus values in the kilopascal range, the present invention provides a material that has an average modulus of above one megapascal.

Example 1

Figure 2:
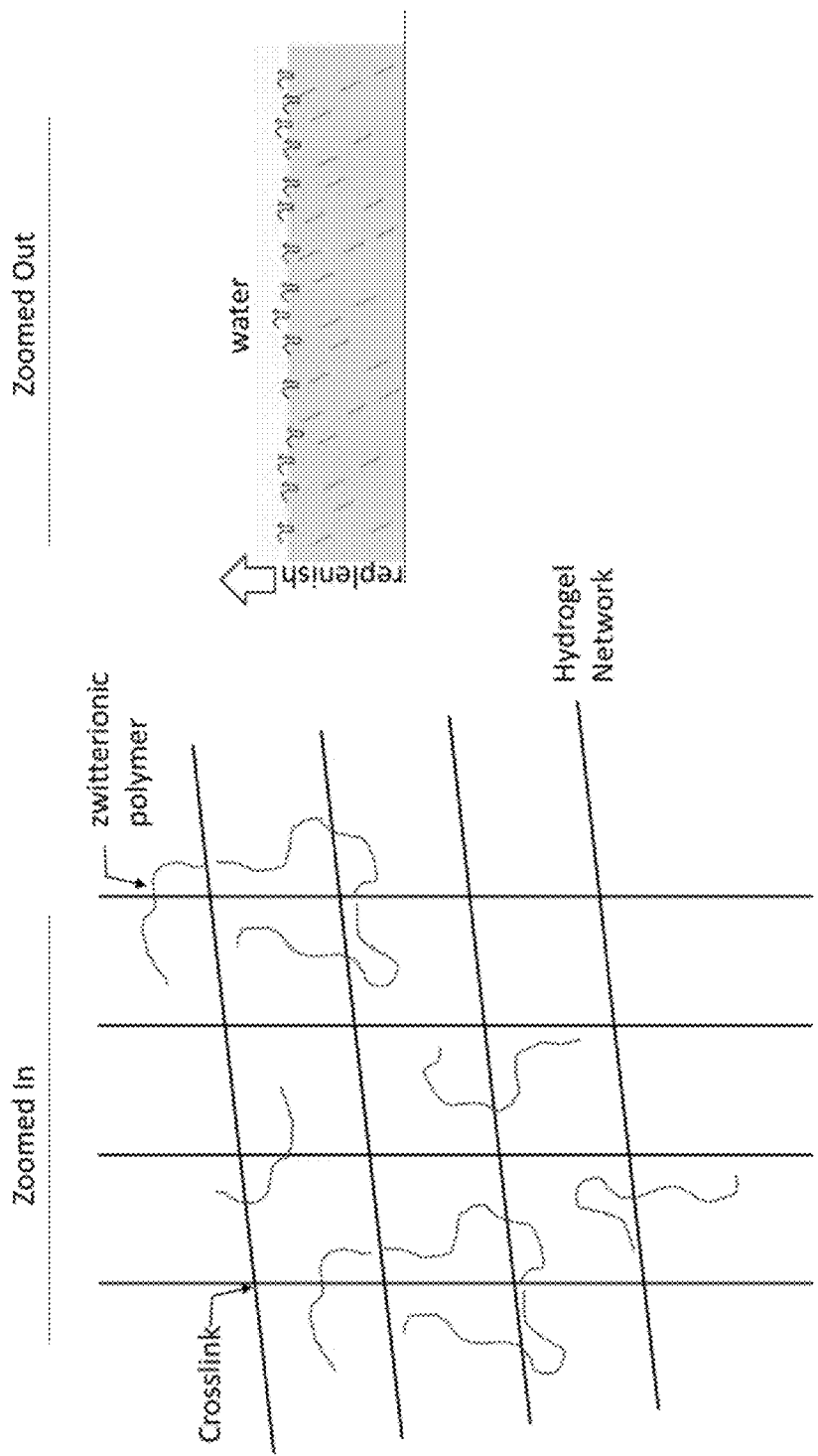

In a first embodiment, the invention comprises the formation of a blend of the hydrogel and zwitterionic polymer to produce a hydrogel with self-lubricating properties. As seen in FIG. 2, this embodiment involves the physical trapping of zwitterionic polymers within the matrix of cross-linked hydrogel. For example, poly(vinyl alcohol) (PVA) (MW=130,000 g/mol) and poly[2-(methacryloyloxy)ethyl]dimethyl-(3-sulfopropyl) ammonium hydroxide) poly (MEDSAH) were selected to demonstrate the invention. poly(MEDSAH) was attained via free radical polymerization, initiated by 2,2'-Azobisisobutyronitrile (AIBN). For the preparation of the PVA-poly(MEDSAH) blends, the desired amount of poly(MEDSAH) was dissolved in DI water and then mixed with PVA to attain a 40 wt % mixture (PVA/DI water). The solution was heated at 90° C. for 6 hours and then subjected to a series of freeze-thaw cycles where the material is frozen at −80° C. for 20 minutes and then left to thaw at room temperature for 30 minutes. Following the freeze thaw process, samples were submerged in water for at least 48 hours to allow for the removal of unbound or weakly bound poly(MEDSAH), as seen in FIG. 3.

Figure 4:
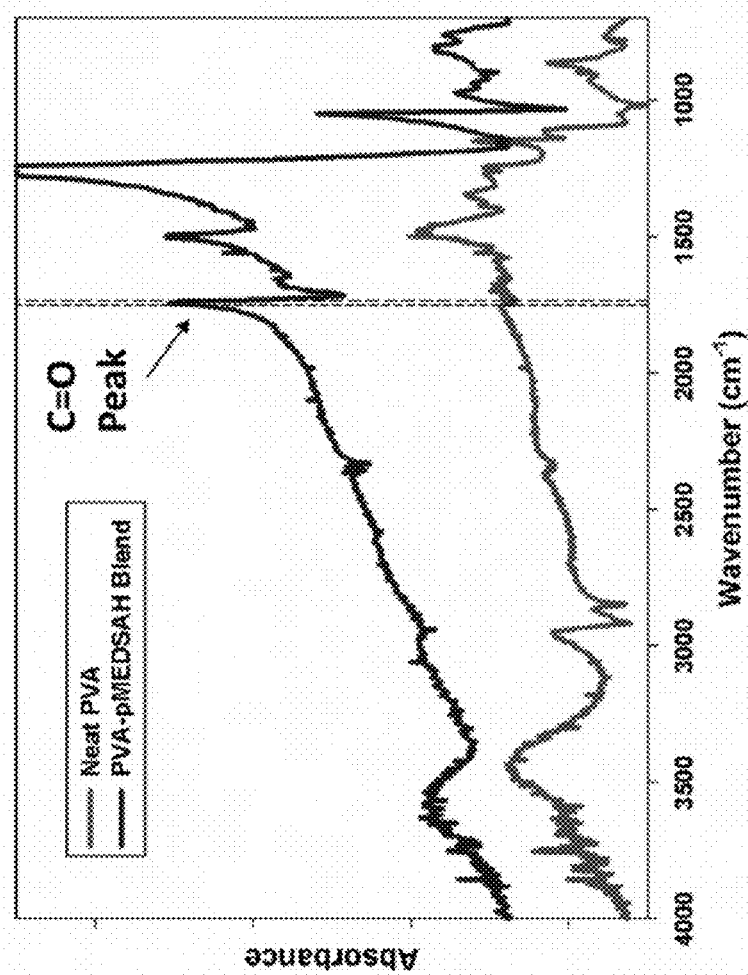
FIG. 4 is a representative ATR spectra of neat PVA and PVA-poly(MEDSAH) blend.
Figure 5:
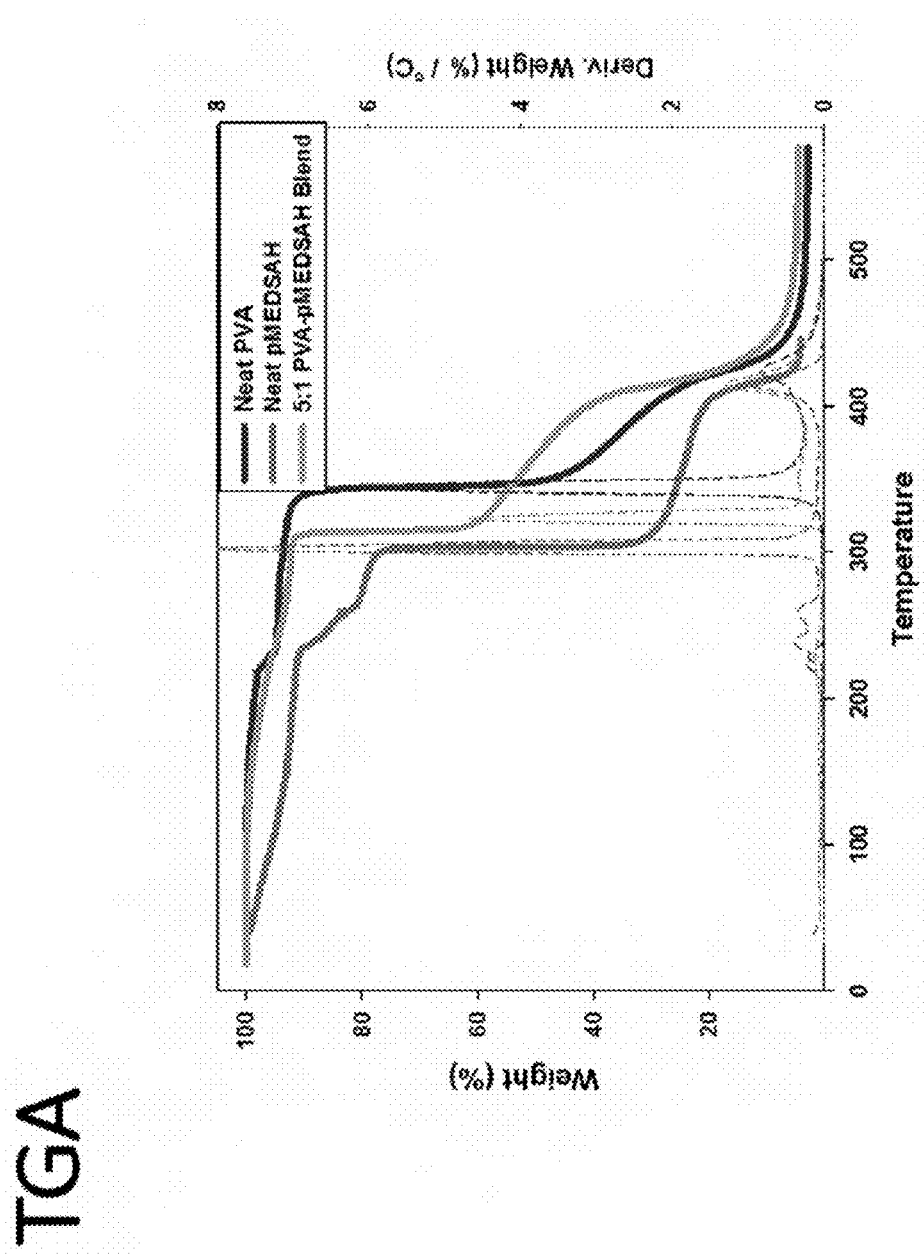
FIG. 5 is a representative degradation profiles of neat PVA and PVA-poly(MEDSAH)poly(MEDSAH) blends.
Figure 6:
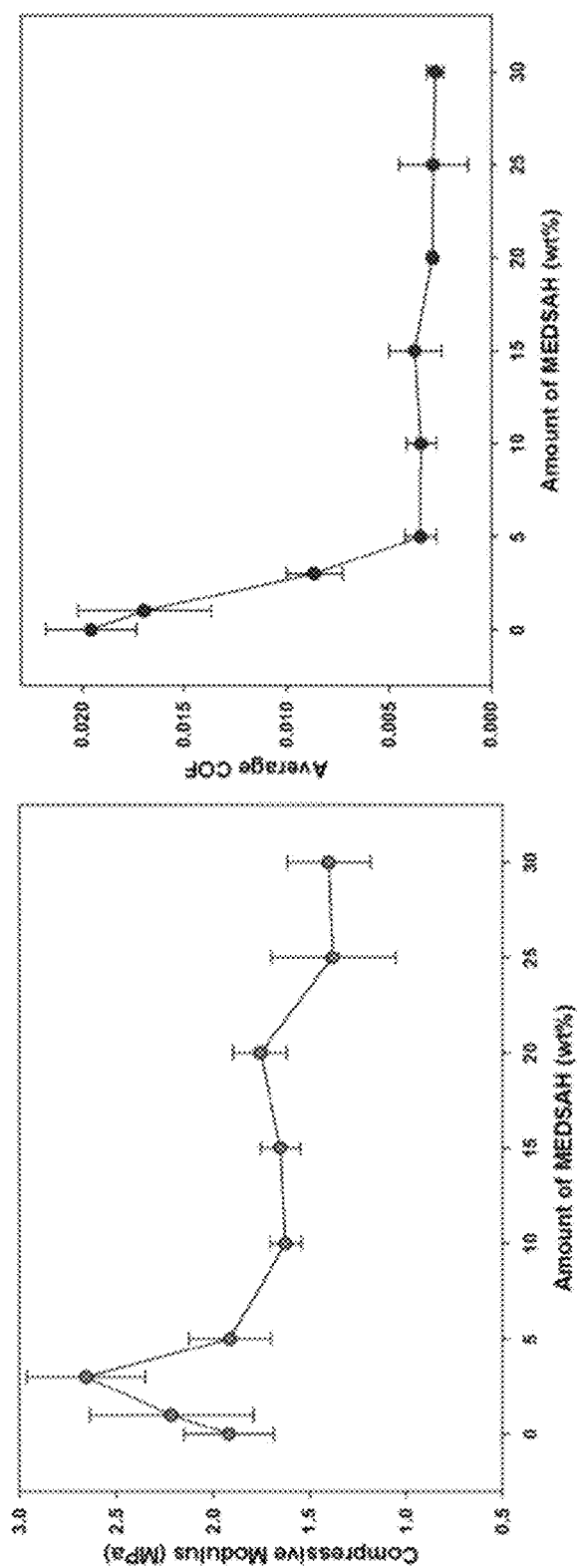
FIG. 6 are graphs of the mechanical (left panel) and tribological (right panel) results for neat PVA and the PVA-poly(MEDSAH) blends with poly(MEDSAH) content ranging from 1-30% MEDSAH.
Figure 7:
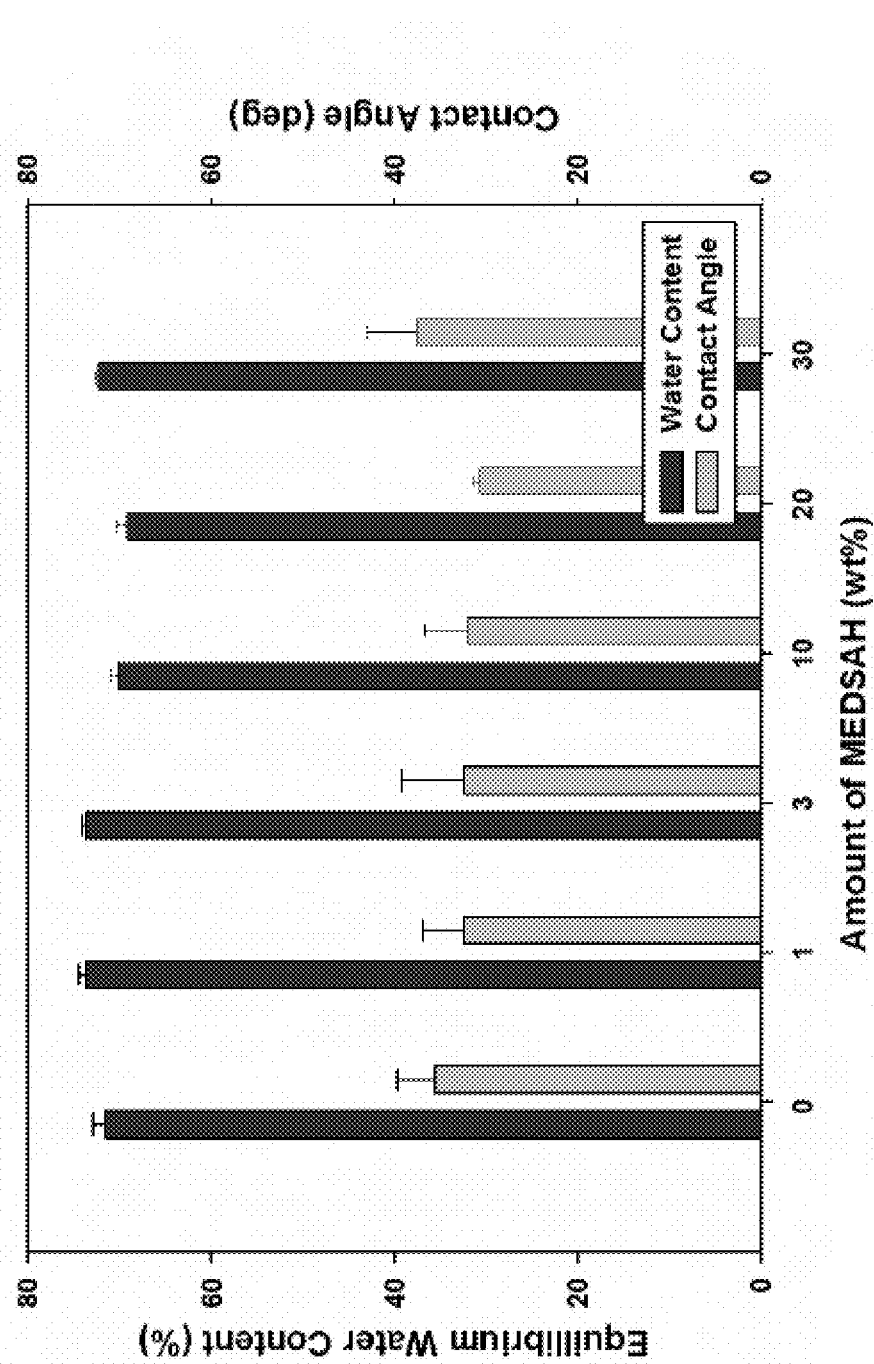
FIG. 7 is a graph of the physical characterization results for the neat and blended material.

Following the solvent exchange process, infrared attenuated total reflection (ATR) was used to qualitatively evaluate the chemical composition of the neat PVA and zwitterionic blend samples. The presence of the ester peak characteristic of MEDSAH as seen in FIG. 4 suggests that poly(MESAH) remains confined to the hydrogel matrix following the solvent exchange process. High resolution thermogravimetric analysis (TGA) was performed to obtain a quantitative estimate of how mush poly(MEDSAH) remained within the blended material following the solvent exchange process. Although the two components that comprise the blends have degradation events separated by about 40° C., rather than exhibiting a distinct degradation event at each temperature point, the blended material exhibits a completely new degradation profile, suggesting that the poly(MEDSAH) is intimately interacting with the PVA hydrogel matrix, as seen in FIG. 5. Referring to FIGS. 6 and 7, results from these experiments suggest that blending PVA with poly(MED-SAH) results in a significant drop in COF (by as much as 80%) while maintaining mechanical and physical properties comparable to the neat material.

More specifically, polyvinyl alcohol (PVA, 99% hydrolyzed) with a reported average molecular weight of 130,000 g/mol was purchased from Sigma-Aldrich (St. Louis, Mo.). The monomer [2-(methacryloyloxy) ethyl] dimethyl-(3-sulfopropyl) ammonium hydroxide) (MEDSAH), solvent N, N-dimethylformamide (DMF) and initiator 2, 2'-azobisisobutyronitrile (AIBN) were also obtained from Sigma-Aldrich. All chemicals were used as received. Neat PVA-H was prepared following the art with some modifications. Solutions were first prepared by solvent casting a 40 wt % (m/v) mixture of PVA and deionized (DI) water. The mixture was heated at 90° C. in an isothermal oven (Fisher Scientific, Waltham, Mass.) for 6 h resulting in a viscous, transparent solution. Stirring was not done during solvent casting due to the high viscosity of the solution and propensity to for bubbles. Following solvent casting, samples were subjected to four freeze-thaw cycles where samples were frozen at −80° C. for 30 min and then allowed to thaw at room temperature for 30 min. This cyclic freeze-thaw process is understood to reinforce the hydrogel structure through formation of crystalline regions, the concentration of these crystalline regions increasing with each successive freeze-thaw cycle. Following the freeze thaw process, samples were submerged in DI water for at least 48 h to ensure they reached equilibrium swelling.

Figure 10:
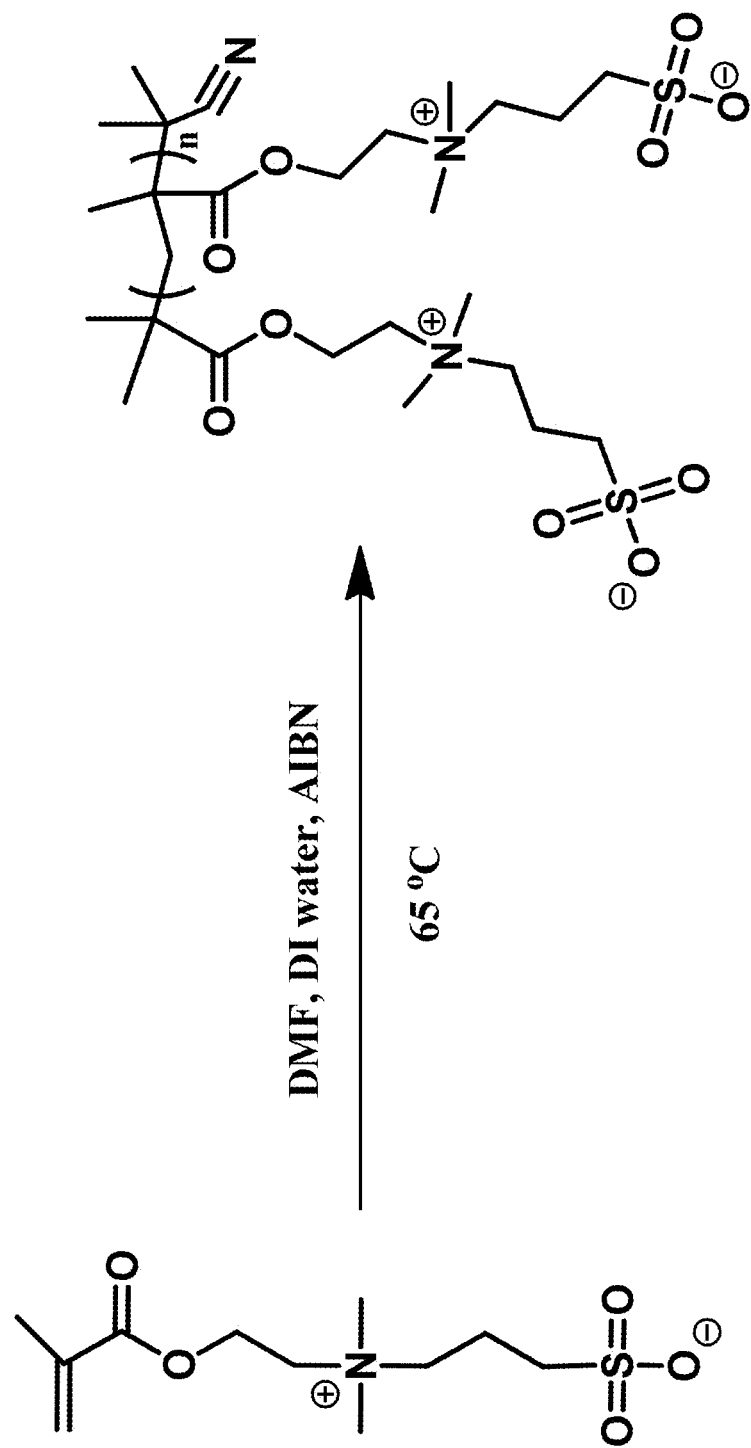
FIG. 10 is a schematic depicting the polymerization of MEDSAH.

Referring to FIG. 10, the zwitterionic polymer poly (MEDSAH) (hereafter pMEDSAH) was prepared through the free radical polymerization of MEDSAH initiated by AIBN under nitrogen in a 60:40 volume ratio of DMF:DI water solution containing 6.7 wt % MEDSAH and a 100:1 monomer to initiator mass ratio (58.78:1 mole ratio). The reaction was performed at 65° C. for 6 h at which point the precipitated product was harvested.

The hydrogel blends were fabricated by initially preparing a 40 wt % (m/v) mixture of PVA to DI water with pMED-SAH contents ranging from 1-30 wt % relative to PVA. pMEDSAH was dissolved in DI water via the assistance of a Vortex-Genie 2 mixer (Scientific Industries Inc., Bohemia, N.Y.). The mixtures were heated at 90° C. for 6 h resulting in a viscous solution. Each solution was then subjected to four freeze-thaw cycles where samples were frozen at −80° C. for 30 min and then allowed to thaw at room temperature for 30 min. Following the freeze-thaw process, samples were submerged in DI water for at least 48 h to allow for equilibrium swelling to be reached. All samples were fabricated in the form of 12 mm diameter discs that were each nominally 5 mm thick. The hydrogel fabrication process is summarized in FIG. 11.

FTIR-ATR was used to quantitatively evaluate the chemical composition of the neat PVA and zwitterionic blend samples with a PerkinElmer AutoIMAGE FTIR-ATR microscope (PerkinElmer Inc., Waltham, Mass.). Neat PVA and zwitterionic blends were placed in contact with a highly reflective germanium crystal. An infrared beam was directed towards the crystal where it reflected off the sample surface and internal faces of the crystal, producing evanescent waves. A portion of this wave energy was absorbed by the sample at wavelength that depends on the chemical composition, while the remaining energy was received by a detector. Absorbance spectra were collected over a range of 450-4000 $cm^{-1}$.

WAXS experiments were conducted to ascertain the crystalline microstructure of the neat and blended material in both dry and hydrated states. For this purpose, a Rigaku S-MAX3000 pinhole camera system was utilized, with a Micromax-007HF rotating anode source operating with Cu Kα emission ($\lambda$=1.5406), voltage of 40 kV and current of 20 mA. Wide-angle scattering patterns were collected at a sample-detector distance of 117 mm, as calibrated using corundum (NIST SRM 676a) with Fujifilm image plates (CR HR-V) and a Raxia-Di Image Plate reader at a scan resolution of 100 µm. An exposure time of 600 s was used for all samples. Samples were prepared for WAXS by slicing the 5 mm thick disks into ~1 mm thick films. Wet samples were maintained in their fully hydrated form by being stored in separate glass vials containing DI water. Samples were mounted in an unconstrained form on the Rigaku sample tray for x-ray scattering analysis. Dry samples were mounted without containment as a film while hydrated samples were contained within a capsule prepared from Kapton® tape. 1D WAXS patterns were plotted as intensity versus the detector angle (2θ).

Hydrogels were submerged in DI water until equilibrium conditions were reached and the equilibrium hydrated mass ($m_w$) was recorded. Samples were then place in a vacuum oven (Isotemp Vacuum Oven, Thermo Fisher Scientific, Waltham, Mass.), until equilibrium was reached and the equilibrium dehydrated mass ($m_d$) was recorded. EWC was computed by calculating the percent difference between the masses of the hydrated and dehydrated samples:

$$EWC = \frac{m_w - m_d}{m_w} \quad (1)$$

Hydrophilicity was evaluated with a ramé-hart advanced goniometer (ramé-hart instruments co., Succasunna, N.J.). Here, contact angle was estimated via the shadow method where a high resolution image of an ultrapure water droplet (EMD Millipore, Billercia, Mass.) was analyzed via the ramé-hares DROPimage Advanced™ software version 2.4.07.

Surface roughness was quantified with a 3D digital microscope (HIROX KH-8700 Digital Microscope, HIROX-USA, Inc. Hackensack, N.J.). Z-stack images were attained from a 100×100 µm field of view with a 1 µm z-step. The surface profile obtained through this approach was then used to compute the RMS roughness using equation 2.

$$R_q = \sqrt{\frac{1}{n} \cdot \sum_{i=1}^{n} (z_i - \bar{z})^2} \quad (2)$$

Where $z_i$ is the individual height measurements over the length of the sample space, n represents the number of height measurements taken, and $\bar{z}$ is the mean value of the individual height measurements. Although there are a number of other methods for measuring surface roughness (including stylus profilometry and atomic force microscopy), non-contact optical profilometry (NOP) has been shown to produce accurate profile measurements when objective lens magnification if greater than 40. Given the simplicity of NOP compared to contact profilometry methods, it is often the method of choice for measuring hydrogel surface roughness when friction experiments are performed on the macro scale.

Figures 3A, 3B, 3C, 3D, 3E:
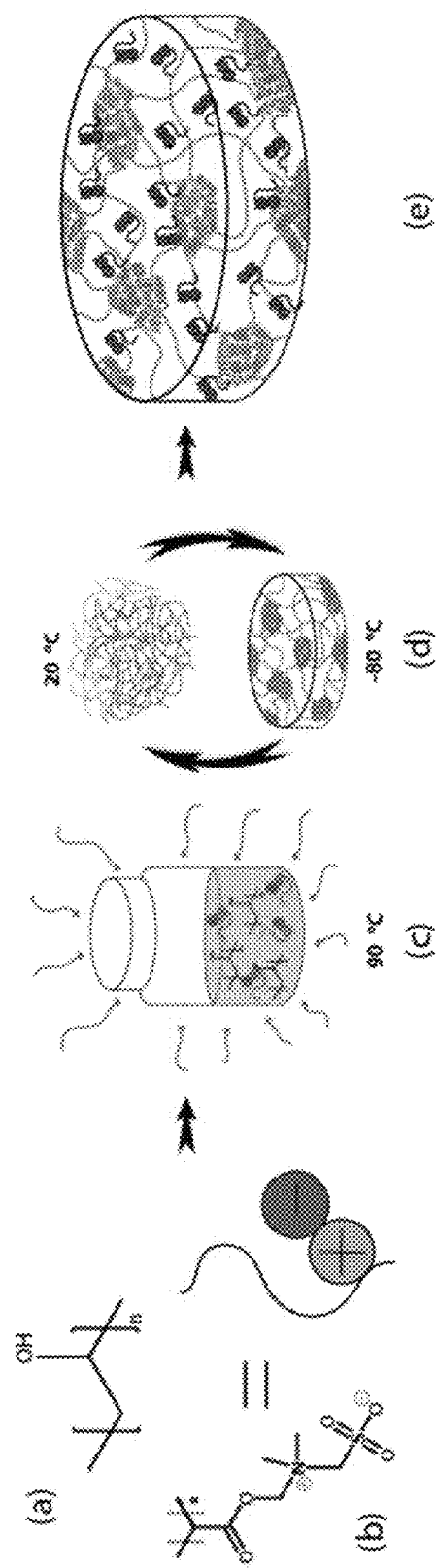

Elastic compressive modulus was determined by performing confined compression experiments using an AR-G2 rheometer (TA Instruments, New Castle, Del.) with an 8 mm diameter flat punch. Confinement was achieved by placing samples in a blind-tapped hole of diameter equal to that of the hydrogels (FIG. 3a). Samples were loaded axially to 10% strain at a strain rate of 10 µm/s, held at 10% strain for 1 minute following compression, and then unloaded at 10 µm/s while monitoring the normal force. Elastic compressive modulus was obtained from the average slope of the initial linear portion of stress-strain curve produced during the unloading step (1-5% strain).

Young's modulus was determined by performing tensile tests on 2.27±0.27 mm thick dog-bone shaped hydrogel films (ASTM Standard D636-03 Type IV, reduced in size four-fold). For tensile testing, a Model 100P Universal Testing Machine equipped with a Biobath chamber and 5.6 lbf load cell was utilized (TestResources, Inc, Shakopee, Minn.). Fully hydrated samples were submerged in saline solution at 37° C. for the duration of the test. For each test, samples were preloaded to 0.1 N before being strained at strain rates ranging from 50-166 µm/s to 10% strain. Modulus was calculated from the average slope over the entire range of the stress-strain curve (0-10% strain).

Observation of the short-term and long-term friction coefficients was performed using an AR-G2 rheometer (TA Instruments) using similar methods to other researchers. Disc-shaped hydrogel samples were press fit into an adapted tribo-rheometry accessory (TA Instruments, FIG. 3) serving as the upper plate. The lower contacting surface was a glass petri dish. A glass petri dish was selected to provide repeatable, low surface roughness. The normal pressure experimental parameter was set at an average of 0.2 MPa. Since the sliding velocity varies along the radial direction, the mid-point of the sample was adopted for velocity calculations (R=12 mm). This relatively high pressure coupled with a constant and relatively slow angular velocity of 0.065 rad/sec was maintained in order to minimize hydrodynamic effects. The torque (T) was measured for a period spanning 5 min to 6 h.

In developing an expression for COF we assumed a uniform normal pressure acting over the sample surface. Thus pressure was expressed as normal force per unit area. The torque that develops the frictional force on the sample was approximated as the measured torque divided by the distance from the center of the rotational axis to the midpoint of the sample surface. Given the definition of COF, the ratio of shear force to normal force, COF was calculated using equation 3.

$$COF = \frac{T}{F_N \cdot R} \qquad (3)$$

PVA-pMEDSAH hydrogels prepared as described earlier were cut into pieces approximately 1-2 mm³ while hydrated followed by complete drying. For determination of cytocompatibility, an extract-based method was employed, based on ISO 10993-5 and ISO 10993-12. To make extracts, dry hydrogel material was weighed out so each sample had 0.1 g/mL extraction media. Materials were extracted in DMEM-F12 (Invitrogen, Carlsbad, Calif.) supplemented with 10% Fetal Bovine Serum (Atlanta Biologicals, Norcross, Ga.) and 1% glutamine-penicillin-streptomycin (Invitrogen, Carlsbad, Calif.). Next, hydrogel samples were rehydrated in extraction media for 72 h until equilibrium was reached. Samples were then sterilized by exposure to ultraviolet light (UV) for 2 h. For extraction, sterile samples were placed in vials with an appropriate amount of media based on the dry mass, sealed and placed on a shaker at 37° C., 60 rpm for 48 h. Following the extraction, media was removed from the sample, to a new tube and frozen at −80° C. until the cell assay. To test the cytocompatibility of pMEDSAH, samples were prepared as previously described, and made into a dry powder which was sterilized by UV as above, and dissolved directly in extraction media (pMEDSAH/media) and allowed to shake at 37° C. for 48 h. As a control, extraction media was allowed to shake at 37° C. for 48 h without sample.

L929 mouse fibroblasts (American Type Culture Collection, Manassas, Va.) were used for this assay, as this cell line is commonly employed for cytotoxicity assays. Cells were grown in the aforementioned media using standard cell culture procedures. L929 mouse fibroblasts were seeded at 25,000 cells/cm² in a 96-well plate. The cells were allowed to attach and spread on the plate for 24 h at which point media was removed and replaced with samples or controls as prepared above. As a negative control, 0.1% sodium dodecyl sulphate (SDS), was made in control media. Following a 24 h incubation, extracts and control media were removed, and replaced with 1/10 volume of CCK-8 solution (Cell Counting Kit-8, Dojindo Molecular Technologies, Inc., Rockville, Md.) which is metabolized by viable cells, turning the media an orange color. This solution was incubated with the cells for 4 h, followed by absorbance reading on a plate reader at 450 nm.

Extracts were prepared from three individual material syntheses as well as three batches of pMEDSAH/media. For the cellular assay, all samples were tested in triplicate. For each assayed batch of material, the mean absorbance was determined for each sample. This absorbance was made relative to the media control, set to 100%. A value greater than 70% viability was an indication of cytocompatibility. The mean percent viability between the three assays was calculated and from this statistical differences between samples was determined.

All statistical analyses was conducted with Minitab 17 (Minitab Inc., State College, Pa.). One way ANOVA with a significance level $\alpha=0.05$ was performed for comparison between the neat and blended material.

Figure 13:
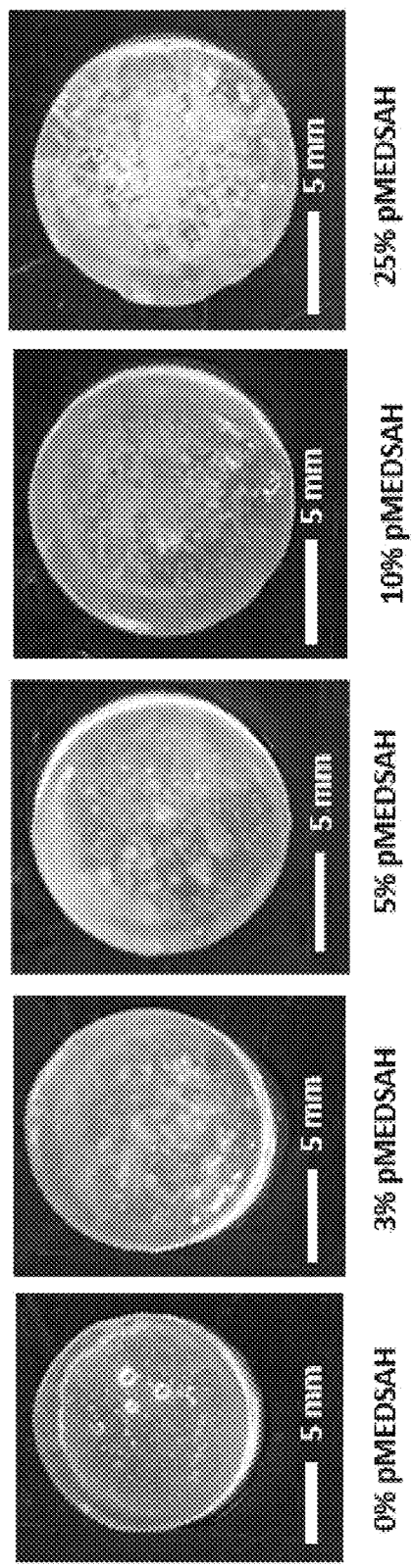
FIG. 13 is a series of representative images of neat and blended hydrogels following solvent casting and freeze thaw cycles

Fabrication of hydrogels via the methods described earlier resulted in a robust hydrogel at all pMEDSAH contents. A slight increase in opacity was observed following the freeze-thaw process. Also, the formation of micron scale pores was observed throughout the bulk material at all levels however the prevalence of these pores generally increased with pMEDSAH content (FIG. 13).

Figure 14:
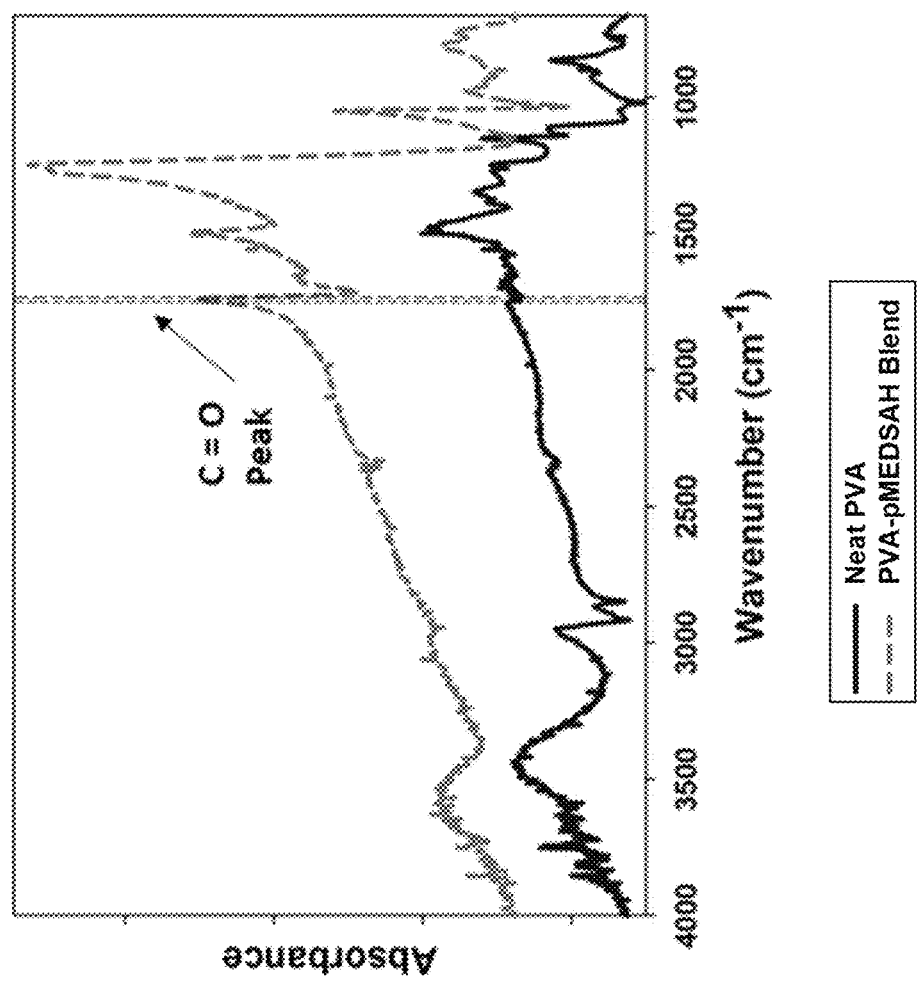
FIG. 14 is a representative FTIR-ATR spectra of the neat and tribologically enhanced hydrogels displaying the ester peak characteristic of MEDSAH.

Fourier transform infrared spectroscopy with attenuated total reflectance FTIR-ATR was used to determine whether or not the zwitterionic polymer remained within the material and was present on the surface after being equilibrated in DI water. The infrared (IR) absorption spectra of neat PVA hydrogels displayed a broad peak spanning 3500-3200 cm⁻¹ characteristic of a hydroxyl (O—H) stretch (FIG. 14). The peaks spanning 3000-2850 cm⁻¹ and 1350-1470 cm⁻¹ are indicative of alkyl (—CH) stretching and bending vibrations. Compared to the IR spectra produced by the neat material, the PVA-pMEDSAH blends display a distinct peak spanning 1735-1750 cm⁻¹ characteristic of carbonyl (C═O)

stretching. In addition we no longer observe the peak spanning 3000-2850 cm$^{-1}$ characteristic of an alkyl stretching vibration. These results suggest that pMEDSAH remains present on the surface of our hydrogels even after being equilibrated in DI water for several days.

The hydrophilicity and swelling behavior of the hydrogels was characterized through measurements of contact angle and equilibrium water content. Results in Table 1 below show that PVA hydrogels with pMEDSAH contents ranging from 1-30 wt % relative to PVA did not yield a significant change in either of these parameters.

TABLE 1

EWC and contact angle data for the neat PVA-H and increasing pMEDSAH concentrations (n = 5, p < 0.05 with neat PVA, ANOVA).

| % pMEDSAH | EWC (%) | θ (deg.) |
|---|---|---|
| 0 | 72 ± 1 | 36 ± 4 |
| 1 | 74 ± 1 | 32 ± 4 |
| 3 | 74 ± 0.4 | 32 ± 7 |
| 5 | 71 ± 1 | 40 ± 12 |
| 10 | 70 ± 1 | 32 ± 5 |
| 15 | 71 ± 1 | 36 ± 5 |
| 20 | 69 ± 1 | 32 ± 1 |
| 25 | 74 ± 1 | 42 ± 7 |
| 30 | 72 ± 0.4 | 38 ± 5 |

An average water content of 71.83±1.51% was observed regardless of the pMEDSAH content. This result falls within the mid-range of reported values for hydrogels fabricated with high molecular weight PVA. A similar result was observed in our water contact angle measurements where contact angle ranged from 32-42° with no apparent trend or significant difference as pMEDSAH content was increased from 1-30 wt % relative to PVA. These measurements are within the standard range for PVA hydrogels.

Figure 15:
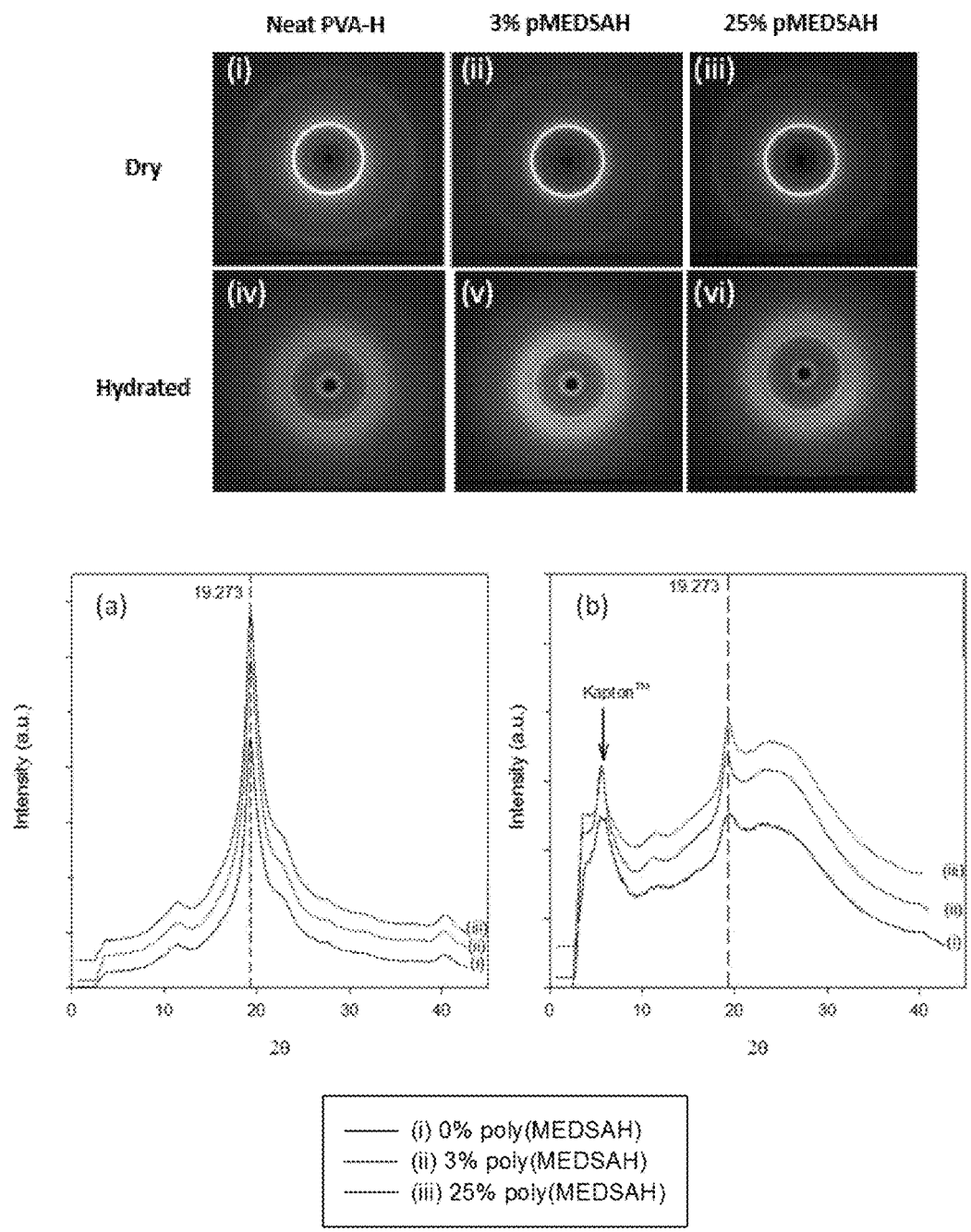
FIG. 15 is a series of graphs showing (top) representative WAXS patterns for dry and hydrated neat PVA-H and PVA-pMEDSAH blends: (i, iv) neat PVA-H; (ii, v) 3% PVA-pMEDSAH blend; (iii, vi) 25% PVA-pMEDSAH blend. (bottom) representative WAXS profiles for: (a) dry, and (b) hydrated PVA-pMEDSAH blends.

The potential for changes to hydrogel microstructure brought about by blending PVA with pMEDSAH was assessed via WAXS of both dry and fully hydrated samples. The WAXS profile produced by dehydrated PVA-H yielded diffraction peaks at 2θ angles of 11.4° (w), 19.3° (s), 23.0° (shoulder), 27.7° (w), 31.5° (w), and 40.3° (s) (w=weak, s=strong). These diffraction peak positions correspond to the monoclinic unit cell structure of crystallized PVA. Diffraction patterns produced from fully hydrated PVA-H yielded an amorphous halo accompanied by a single diffraction ring at 2θ=19.4° (very close to the dry hydrogel). A low angle peak characteristic of the Kapton® window was also evident. The strongest peaks in both cases correspond to a d-spacing of 4.59 Å. Although hydrogels prepared in this investigation were formed from solutions that were significantly more concentrated than other studies that have evaluated PVA-H microstructure via WAXS, these result agree quite well with results from the low wt % gels. WAXS experiments were also performed on PVA-pMEDSAH blends at the 3% and 25% pMEDSAH levels to assess whether or not trends observed in terms of elastic compressive modulus (discussed below) were attributed to changes in the hydrogel microstructure. In comparing the profiles from FIG. 15b, there are not any changes in the WAXS patterns, indicating that the blended material continues to diffract x-rays in a similar manner compared to the neat material. This suggests that pMEDSAH does not alter the hydrogel microstructure at either of these levels.

Results from the confined compression experiments (FIGS. 16a and 16b) show that blending PVA with as much as 30 wt % pMEDSAH does not diminish the compressive stiffness of the hydrogel matrix. Rather than observing a steady decline in compressive modulus as pMEDSAH content was increased, we consistently observed a peak in modulus at 3% pMEDSAH that is statistically higher (p<0.05) than that of the neat material. This peak at the 3% level was followed by a slight but steady decrease as pMEDSAH content was increased further, though never dropping below 1.38±0.39 MPa. The confined compressive modulus of neat PVA was found to be 1.92±0.26 MPa which is within the reported range for neat PVA-H. Compressive modulus for the blended material containing 1-30 wt % pMEDSAH ranged from 2.66±0.34 MPa to 1.38±0.39 MPa.

Tensile tests were performed on hydrogel films to determine whether or not the peak compressive modulus observed at 3 wt % pMEDSAH also exists in tension. Results from these experiments showed that this was not the case (FIG. 16c). Instead, as PMEDSAH content was increased we observed a trending decrease in Young's modulus at a 166 μm/s strain rate, and no apparent trend at a 50 μm/s strain rate. Confined compression tests were also performed on hydrogel films of the same thickness as required for tensile testing to determine whether or not the fabrication process to yield thinner freeze-thaw gels, itself, influenced the trend we observed on the thicker gels used for the friction experiments. Results from these experiments revealed a slight decrease in compressive modulus across the board; however, a similar trend was observed (FIG. 16b) for the two thicknesses. We did find that blending PVA with pMEDSAH appears to increase the elastic nature of the hydrogel matrix. An increase in the strain rate from 50 μm/s to 166 μm/s yielded a significant increase in the apparent Young's modulus of the neat PVA-H films (p<0.05); however, this viscoelastic behavior appears to be suppressed as pMEDSAH content is increased. The relative change in Young's Modulus in response to the strain rate ranged from 48% in the neat material to 2% in the 25% pMEDSAH blends.

Figure 8:
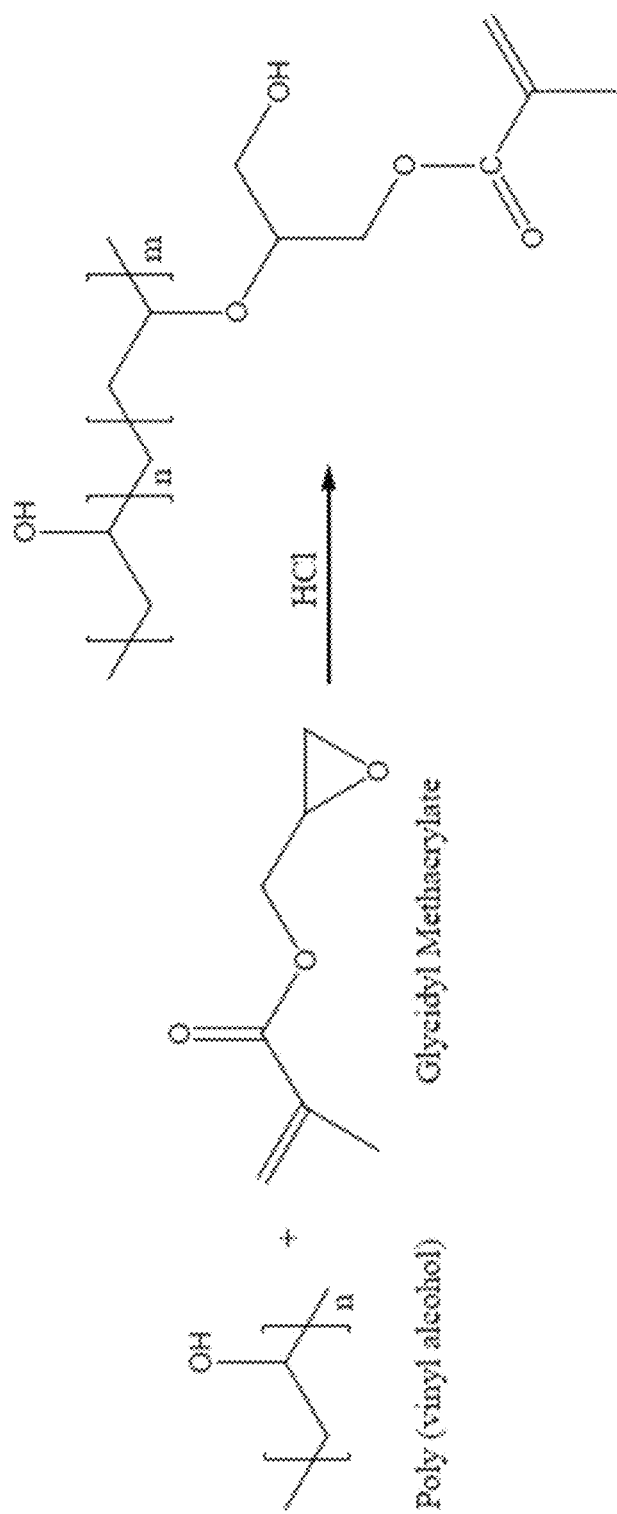
FIG. 8 is a schematic of the synthesis of methacrylate modified PVA (MPVA)
Figure 9:
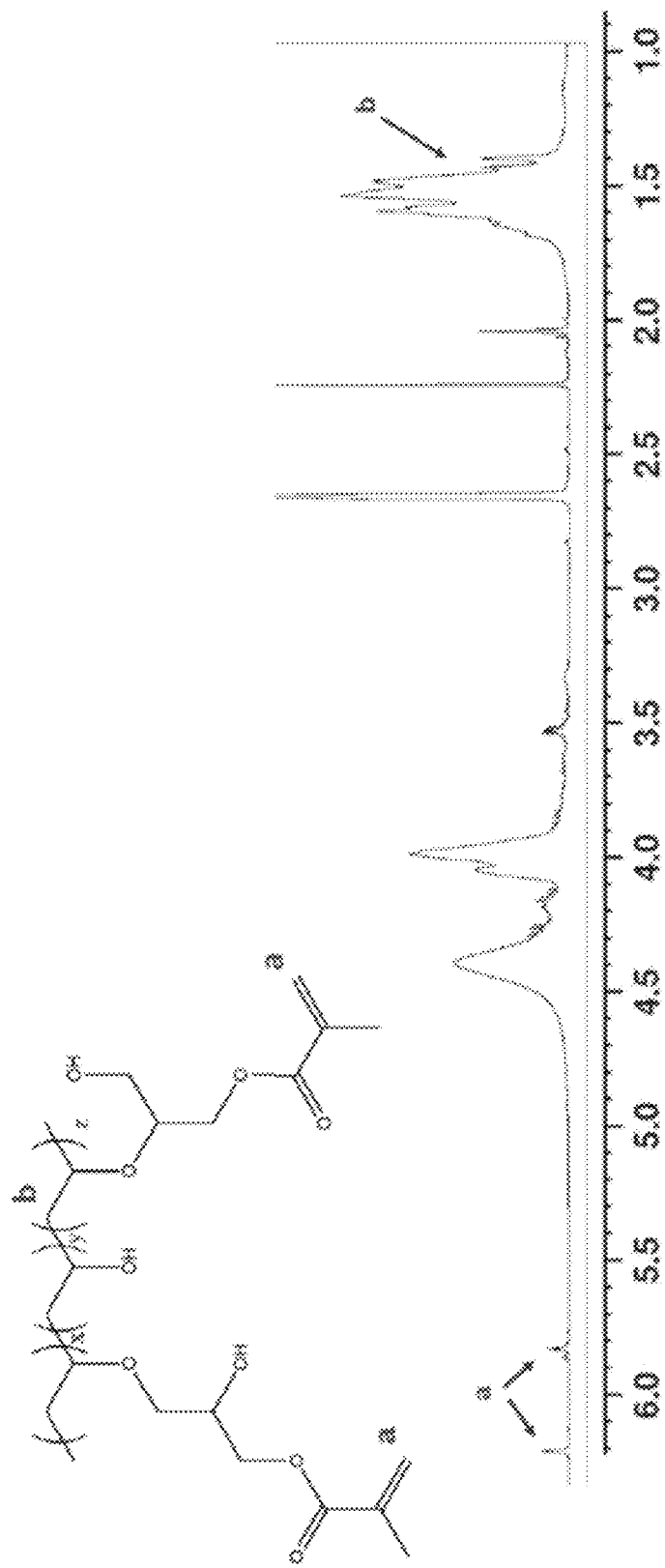
FIG. 9 is a representative 1H NMR spectra of MPVA, where percent modification was estimated by taking the ratio of terminal vinyl protons (a) to the methylene protons on PVA (b)

Comparison between neat PVA-H and the zwitterionic blends revealed that blending PVA with pMEDSAH resulted in a significant reduction in average COF (FIGS. 8 & 9). This significant decrease in COF was observed with as little as 3 wt % pMEDSAH relative to PVA. With 5% pMEDSAH a saturation point appears to be reached in terms of reducing COF. Average COF decreases from 0.136±0.015 for the neat material down to 0.024±0.009 at the 5% level. The lowest coefficient of friction was observed for 30 wt % pMEDSAH which displayed a COF of 0.019±0.003.

Six-hour friction experiments were performed to investigate the stability of the lubricative properties observed in our five minute experiments. Results in FIG. 9 show that the significant reduction observed in our five minute experiments were maintained over a 6-hour period. In addition, the blends displayed a steady decrease in COF over the first 1-2 h of the experiment before reaching a steady value. On the other hand, neat PVA-H generally displayed a steady increase in COF over the first hour of the experiment before reaching a steady value.

When evaluating the tribological properties of any material, surface roughness is an important parameter to consider. Characterization of the surfaces of hydrated neat and blended material via 3D digital microscopy yielded RMS values ranging from 0.36±0.25 μm to 0.66±0.48 μm with no apparent trend or significant difference as pMEDSAH content was increased. Based on this result we postulate that the significant reduction in coefficient of friction can be attributed to hydration lubrication brought about by the zwitterionic polymer rather than a chance in surface topography.

Figure 19:
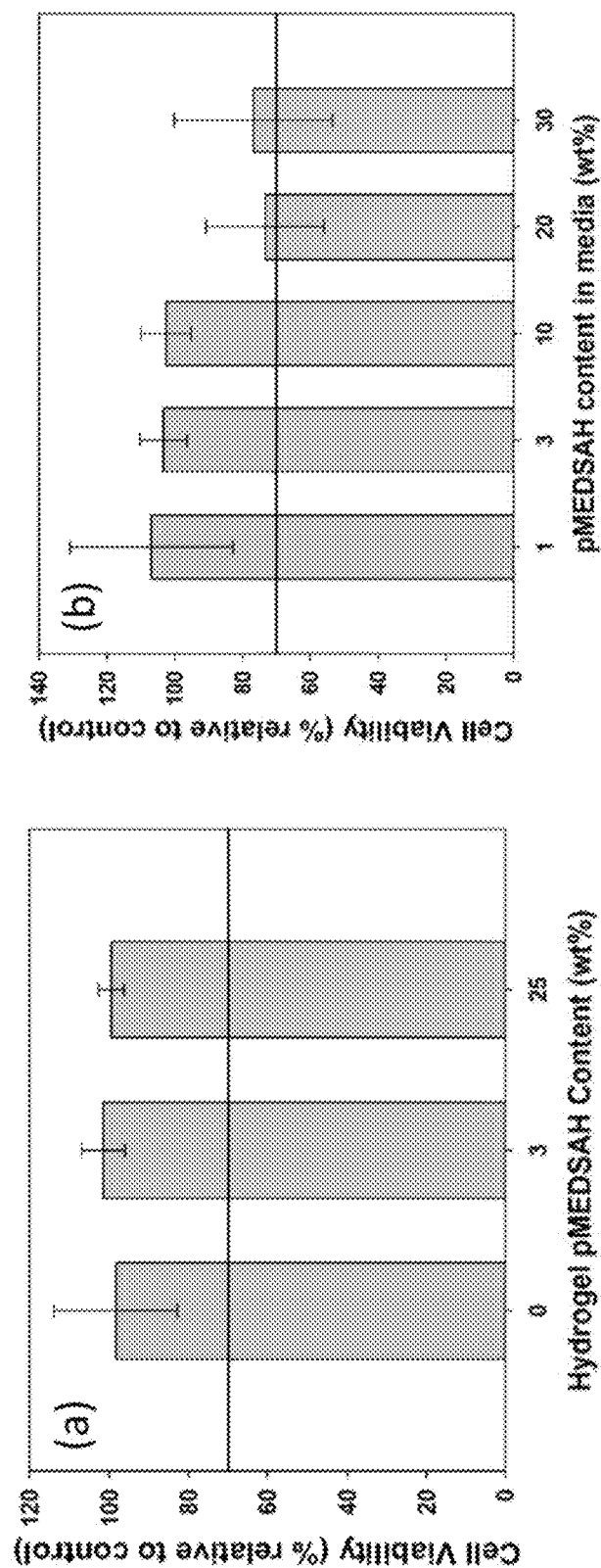
FIG. 19 is a graph of the cytocompatibility of L929 cells in extracts generated from (a) Neat PVA hydrogel and hydrogel samples with 3% or 25% pMEDSAH, (b) pMEDSAH dissolved in media at various concentrations, where data is representative of the mean cell viability (±SD) for three material samples, assessed in three cell-based assays.

Cytocompatibility of pMEDSAH was assessed by dissolving the weight percentage of pMEDSAH associated with each blend level (see Section 2.2.3), and incubating for 48 h. When L929 cells were cultured in the pMEDSAH, it was determined that at all pMEDSAH concentrations, the cells are highly viable (FIG. 19a). Higher levels of pMEDSAH resulted in a trend towards lower viability which, however, was not statistically significant. In a similar study, neat PVA and PVA-pMEDSAH blends were found to be cytocompatible (FIG. 10b), with viability levels well above the 70% threshold indicative of cell viability. These data demonstrate that our materials are cytocompatible, and lay the ground work for future work with the materials in cellular environments as substrates for cell culture as well as for implant studies where the materials are in contact with body tissues.

Thus, a novel material was prepared by blending zwitterionic polymer, pMEDSAH, with PVA, a widely used biocompatible hydrogel. Freeze-thaw PVA-H was selected as the base polymer of choice due to its well-established biocompatibility, low protein absorption and mechanical strength. In addition, these hydrogels have been approved by the FDA for use as drug delivery systems, contact lenses, membranes, and orthopedic devices. Other biomedical applications of PVA-H include artificial corneal, vascular grafts, and nucleus pulposus replacement.

Figure 17:
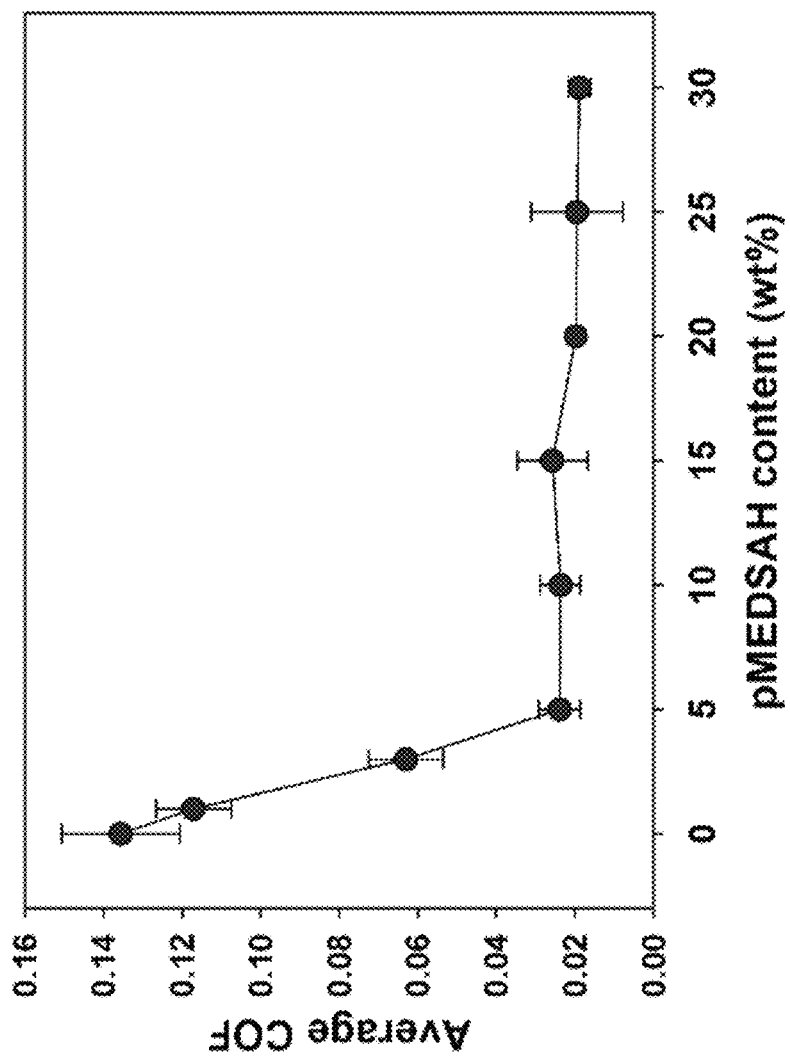
FIG. 17 is a graph showing friction data for hydrogels with increasing pMEDSAH concentrations (n=5, *p<0.05 with neat PVA-H, ANOVA)
Figure 18:
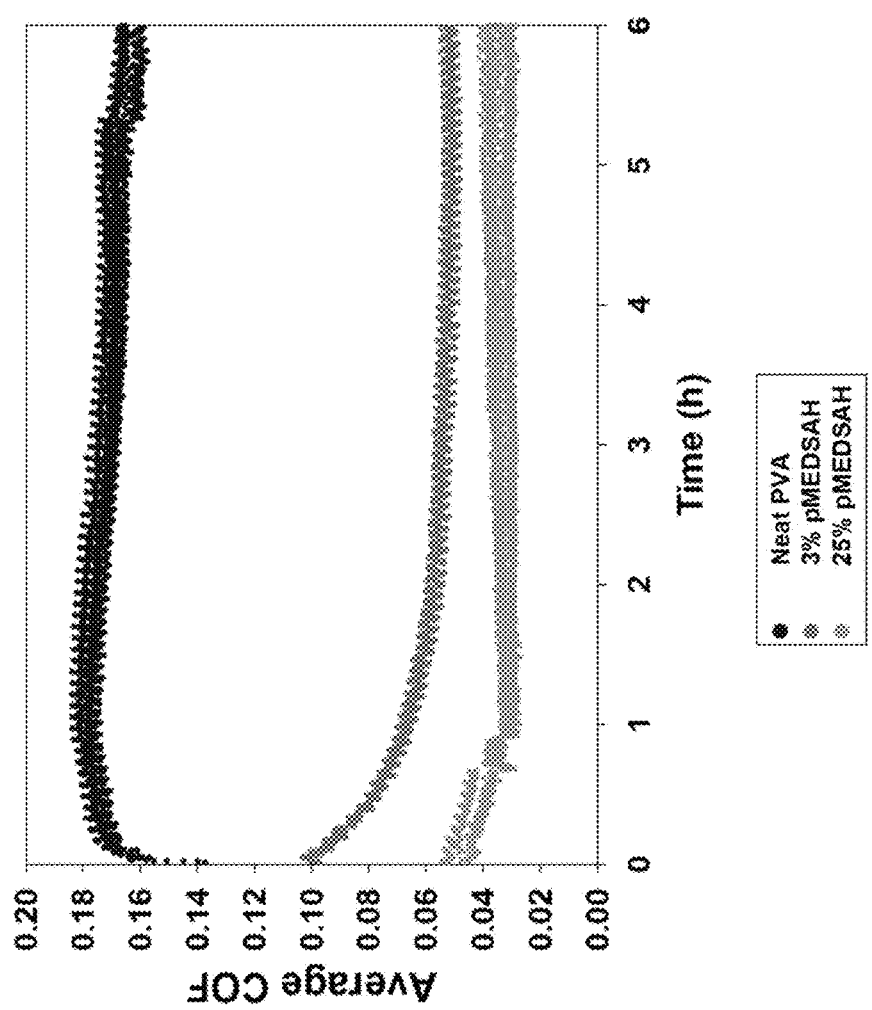
FIG. 18 is a graph of representative plots of COF vs time for the neat and blended material over the course of 6 h experiments.
Figure 20:
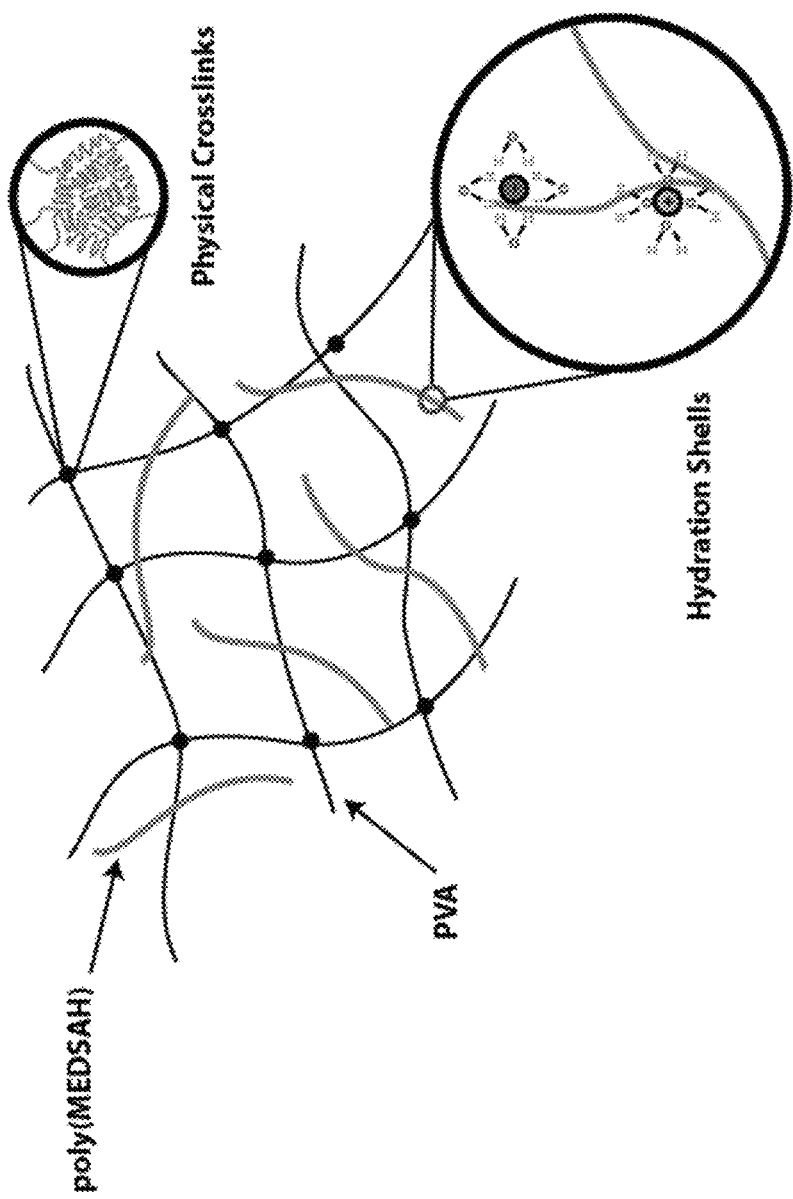
FIG. 20 is a schematic illustrating the proposed boundary lubrication mechanism fostered by the zwitterionic polymer at the surface and with interstitial mobility within the crosslinked hydrogel.
Figure 21:
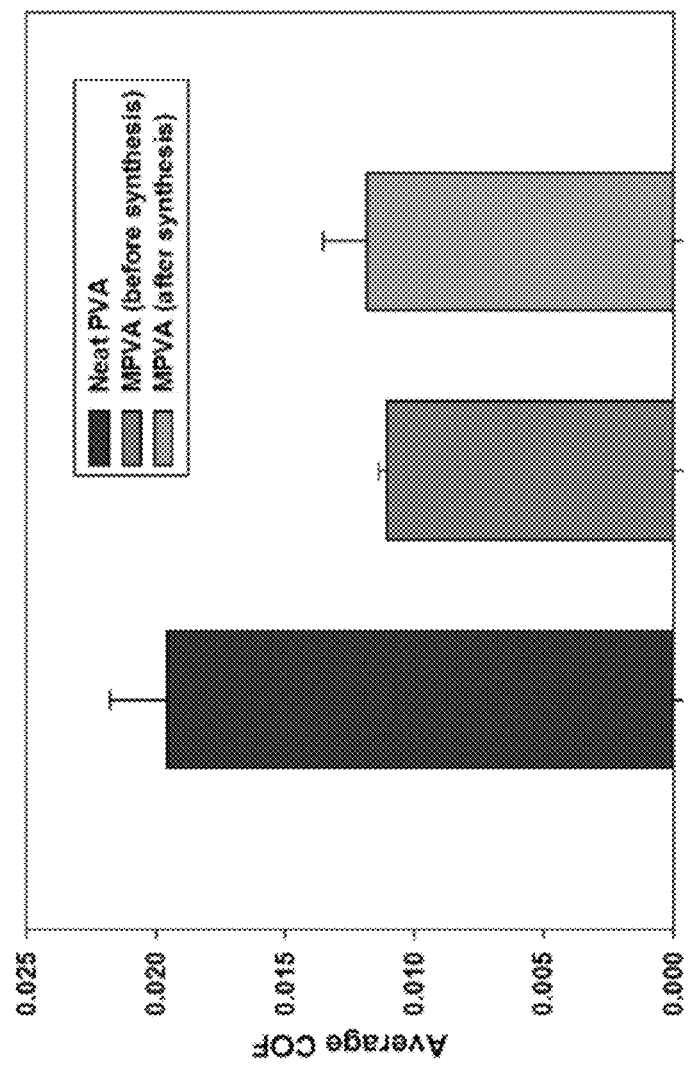
FIG. 21 is a graph of the tribological characterization results for the second embodiment of the present invention.
Figure 22:
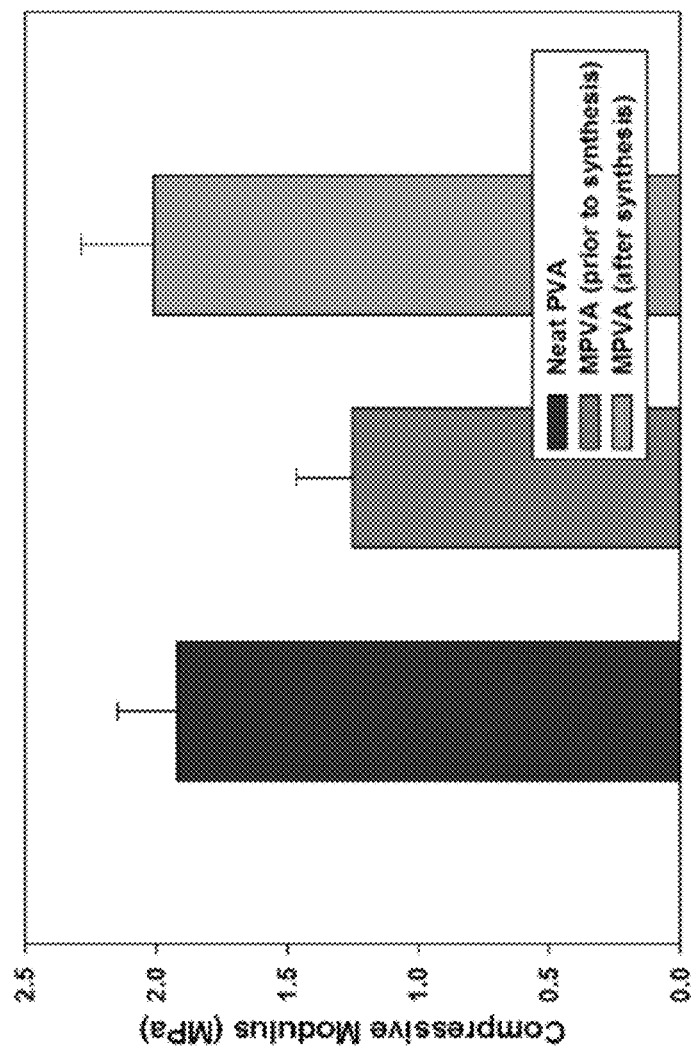
FIG. 22 is a graph of the confined compression results for the second embodiment of the present invention.
Figures 23A, 23B, 23C, 23D:
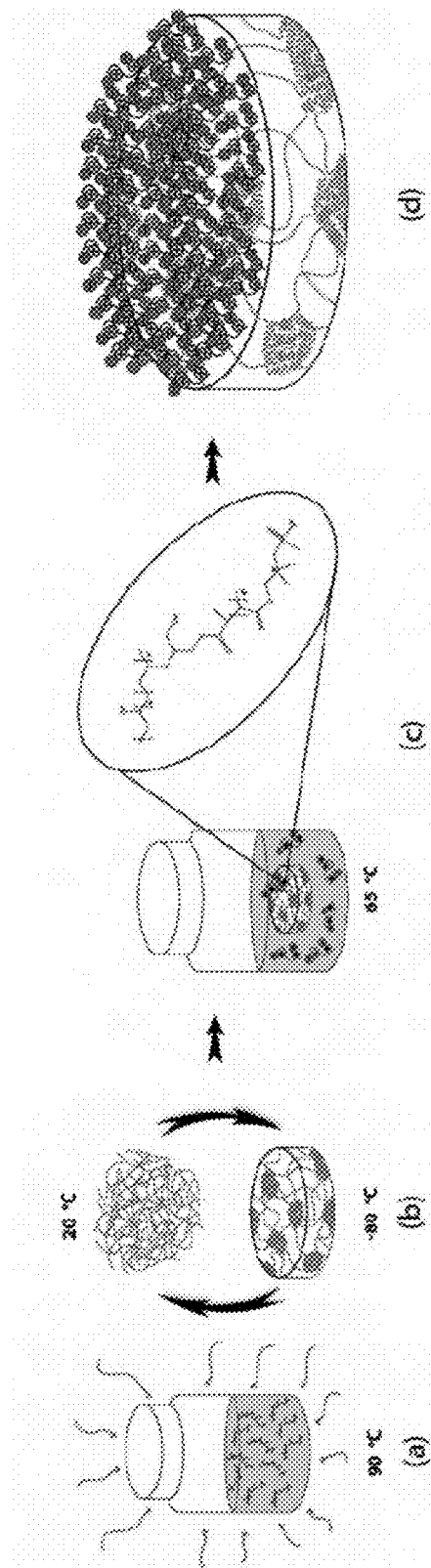
FIGS. 23($a$) through 23($d$) is a schematic of the fabrication of brush functionalized PVA hydrogels, showing: (a) the solvent casting of MPVA; (b) the freeze thaw process; (c) brush functionalization; and (d) the viable structure for the brush functionalized material.

The data displayed in FIGS. 17 and 18 show that the addition of as little as 5% pMEDSAH results in as much as an 80% reduction in COF. This result can be attributed to hydration shells forming around the charged groups on the pMEDSAH; namely the negatively charged sulfur trioxide group ($SO_3^-$) and the positively charged quaternary ammonium group ($NR_4^+$). Due to their dipole, water molecules are strongly attracted to the charged groups on pMEDSAH resulting in the formation of molecular scale $H_2O$ films on the hydrogel surface. Unlike non-associating liquids which exhibit solid-like properties under high pressures, these hydration films are able to maintain their fluidity providing a fluid-like response under high pressure. This yields a reduction in the development of shear stress between the opposing surfaces and a drop in coefficient of friction. Although further investigations are needed to fully understand this mechanism in order to design and possibly control a hydrogel material with a very efficient boundary lubrication system, the results observed in this investigation indicate that blending pMEDSAH with PVA significantly enhances the materials lubricity through hydration lubrication, depicted schematically in FIG. 20.

Figure 16:
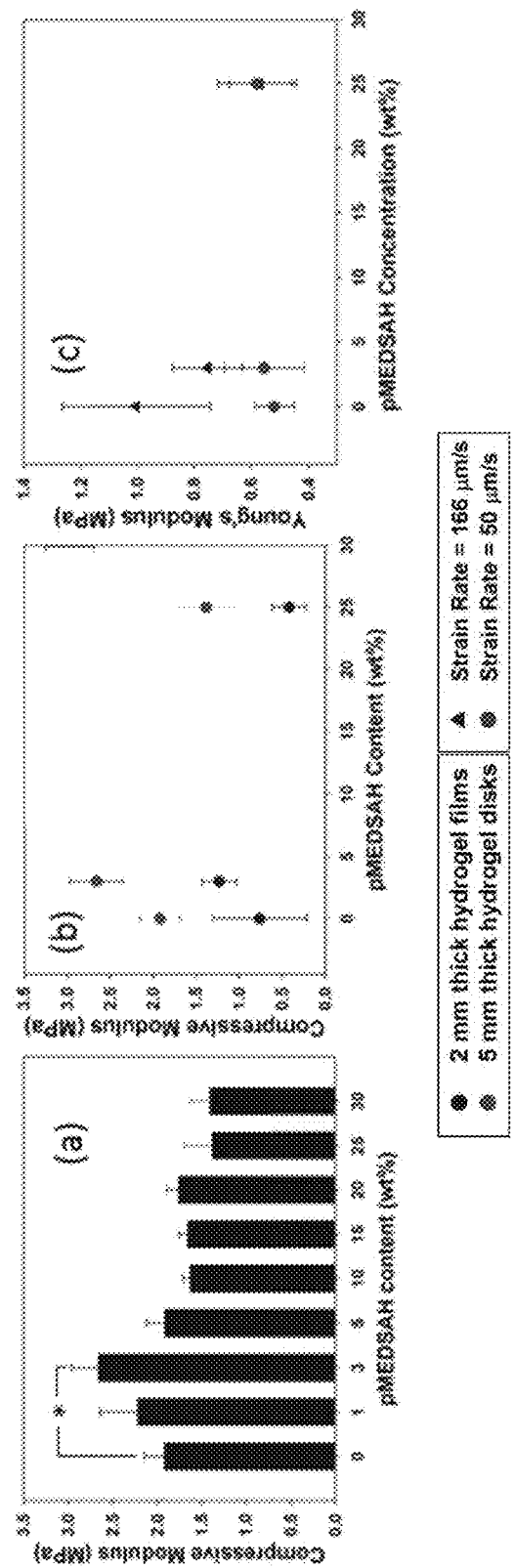
FIG. 16 is a series of graphs showing the characterization of (a) compressive modulus of the hydrogel discs used in the COF experiments (b) compressive modulus of the hydrogel discs compared to hydrogels fabricated as films and (c) Young's modulus for neat and blended hydrogels (n=5, *p<0.05 with neat PVA-H, ANOVA)

Results from the confined compression and tensile experiments indicate that the reduction in COF can be achieved without significant compromise to the mechanical properties of the neat material (FIG. 16). Mechanical strengthening of freeze-thaw PVA hydrogels is understood to be dictated by the formation of physical crosslinks. At low concentrations, blending PVA with pMEDSAH appears to result in stiffer hydrogels, possibly due to a secondary interaction between the two polymers. When pMEDSAH content exceeded 3 wt % we observed a trending decrease for both tensile and compressive deformations. Above this threshold concentration, pMEDSAH may inhibit the formation of physical crosslinks between PVA molecules, resulting in the observed decrease in mechanical stiffness. Crosslinking capability affects the volume fraction of water present in the hydrogel which, in turn, alters the rigidity of the system reflected in the measured elastic modulus. Nevertheless, results from our physical characterization did not reveal any significant changes or trends in equilibrium water content (Table 1) or hydrogel crystallinity (FIG. 15), suggesting that the changes in physical crosslinking may occur at constant overall crystallinity.

Results from our physical characterization also suggests that the pMEDSAH molecules may freely diffuse within the hydrogel matrix. This mechanism also appears to be at work in our friction experiments where, unlike in the neat material where we observe a steady increase in COF followed by a plateau, blends containing 3% and 25% displayed a steady decrease in COF over time, followed by a plateau. This behavior may be caused by the gradual elution of pMEDSAH from the bulk to the surface of the hydrogel, an area of current inquiry.

One major area of potential for these zwitterionic blends is in the repair of focal chondral defects. Numerous researchers have considered PVA-H as a synthetic implant to repair articular cartilage damaged by injury or disease. Considerable effort has gone into characterizing and improving PVA-H mechanical stability. Thus PVA-H is considered to have suitable tensile and compressive mechanical properties to be able to function as a cartilage or meniscus implant. Although these PVA-H successfully replicate the fluid pressurization mechanism exhibited by the natural tissue, they often fail to replicate surface boundary lubrication mechanisms brought about by proteoglycan-synovial fluid interactions. Investigations that have sought to improve the tribological properties of PVA-H include the fabrication of PVA-polyvinyl pyrrolidone blends, and surface functionalization of a hydrophobic boundary lubricant molecule. Based on the results of the present invention, blending PVA with pMEDSAH appeared to result in a very effective approach for enhancing the tribological properties of PVA hydrogels while preserving desirable mechanical properties comparable to the neat material.

Thus, this embodiment of the present invention provides an excellent platform for significant enhancement of the tribological properties of PVA hydrogels within the boundary lubrication regime while maintaining the inherent physical and mechanical properties of the starting material.

Example 2

In a second embodiment, the present invention comprises the use of surface initiated polymerization to form the improved hydrogel. End-grafting of nanometer scale polymer brushes is a widely used approach for the modification of surface properties and can be accomplished through surface initiated polymerization. Initiators are attached to the surface of interest, allowing the polymer chains form a covalent bond, and then the polymer brushes are grown from the initiator site. For example, poly(vinyl alcohol) (PVA) (MW=130,000 g/mol) and poly[2-(methacryloyloxy) ethyl] dimethyl-(3-sulfopropyl) ammonium hydroxide) poly (MEDSAH) were selected for use in demonstrating the present invention. The presence of the hydroxyl group on the PVA will not likely allow for the formation of a covalent bond to poly(MEDSAH). Therefore, PVA was first functionalized to glyicidyl methacrylate (GM) before it was crosslinked to form a methacrylate modified hydrogel. It is also expected that the presence of the vinyl groups associated with GM will allow the poly(MEDSAH) to covalently bind to the surface of the methacrylate modified PVA hydrogel. Methacrylate modified PVA (MPVA) was prepared via the esterification of the pendent alcohol group associated with the PVA repeat unit, as seen in FIG. 8. NMR spectroscopy was used to verify that ~5% modification was attained, as seen in FIG. 9. Once MPVA had been successfully synthesized, a 40 wt % MPVA-DI water mixture is prepared and then heated at 90° C. for 6 h. Following the heating process, samples were subjected to a series of freeze thaw cycles where they were frozen at −80° C. for 20 min and then left to thaw at room temperature for 30 min. This process results in the formation of an MPVA hydrogel.

Figure 11:
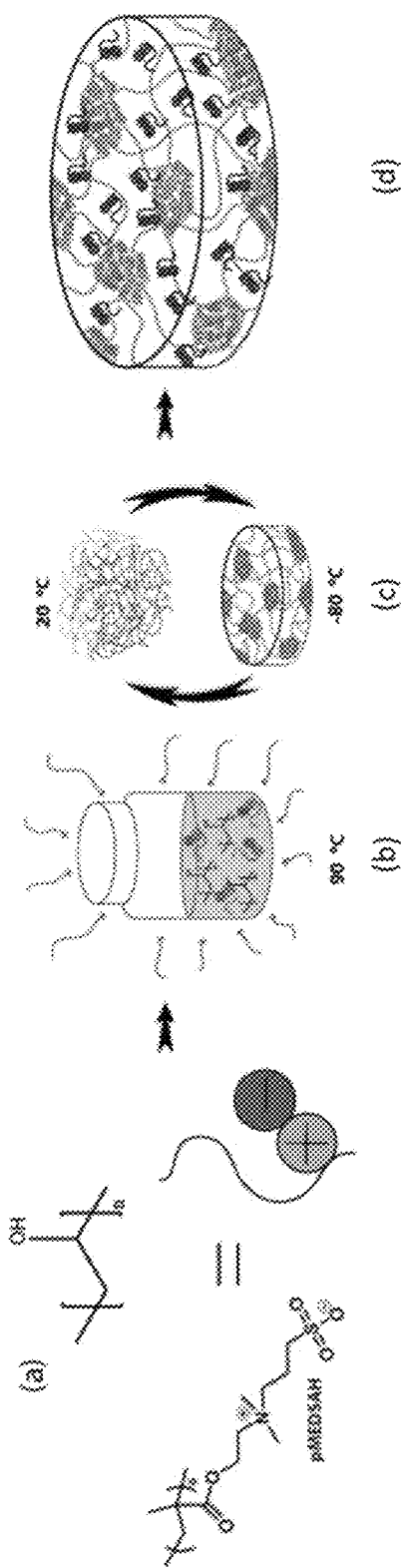
FIG. 11 is a schematic of hydrogel fabrication procedure: (a) Structure of PVA and a cartoon depiction of pMEDSAH, (b) Illustration of heating PVA-pMEDSAH solution, (c) Hydrogel crosslinking and (d) Final product.
Figure 12:
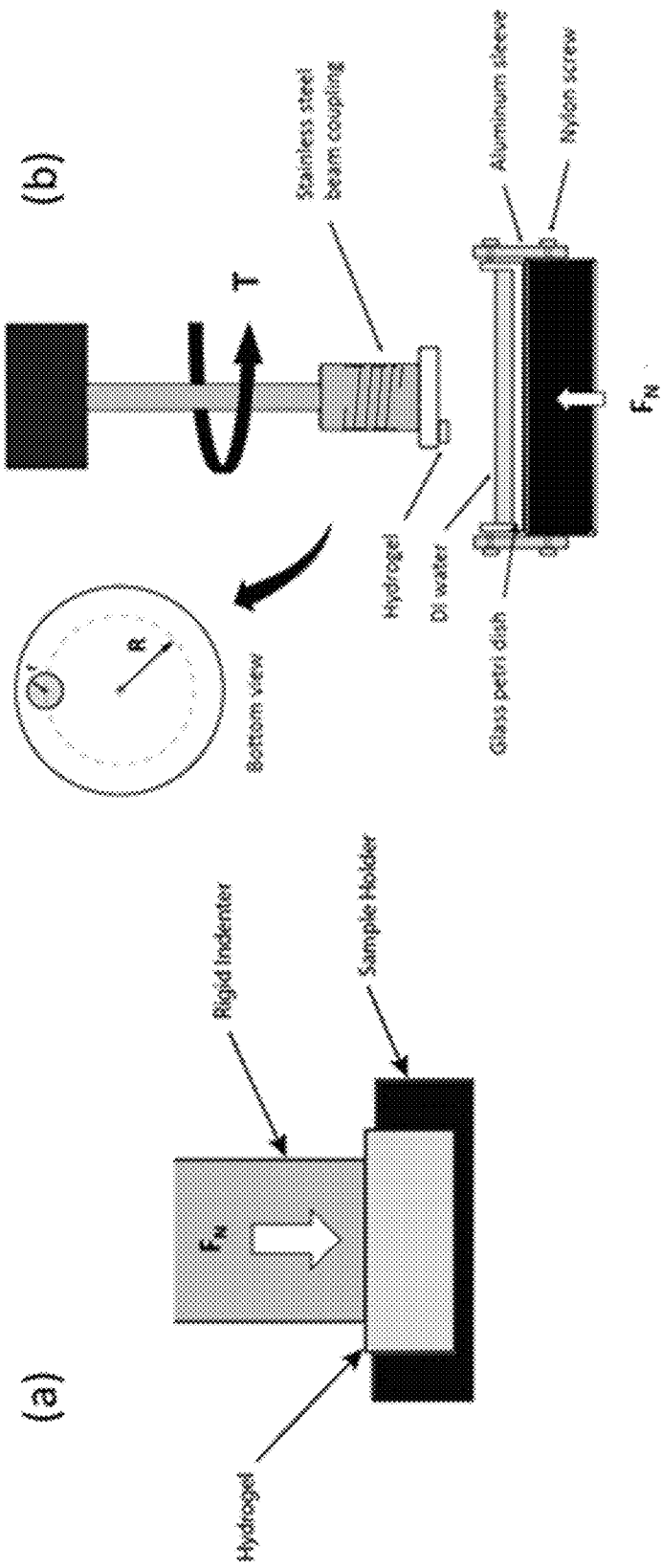
FIG. 12 is a schematic illustrating the (a) confined compression and (b) tribo-rheometry experimental setup.

Following the solvent casting process, samples were dehydrated and then swelled in a DI water solution containing free radical initiator, 2,2'-Azobis(2-methylpropionamidine) dihydrochloride (AAPH). Once equilibrium was attained, samples were then submerged in an aqueous MEDSAH-DI water solution at 56° C. for 6 hours, resulting in surface initiated polymerization of poly(MEDSAH). This synthesis may be verified via $^1$H-NMR. Referring to FIGS. 10 and 11, a preliminary mechanical and tribological characterization indicates that the brush approach of this embodiment decreases the coefficient of friction (COF) of the hydrogel.

Alternative approaches to this EXAMPLE 2 as means to obtain surface initiated polymerization of zwitterionic polymers are envisioned, including grafting of a controlled radical polymerization initiator to PVA, followed by controlled radical polymerization of MEDSAH exclusively from those initiation sites. Here, examples of controlled radical polymerization include atom-transfer radical polymerization (ATRP), nitroxide-mediated polymerization (NMP), and reversible addition-fragmentation chain transfer polymerization (RAFT).

Figure 24:
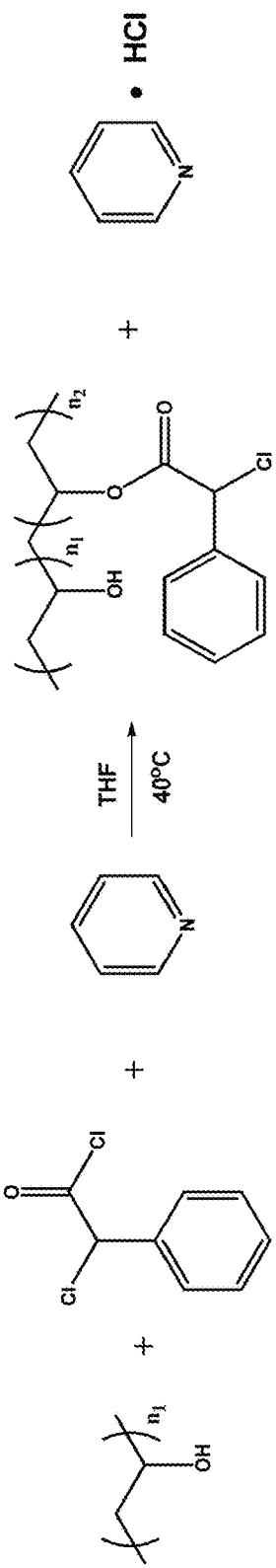
FIG. 24 is a schematic showing grafting of ATRP initiator α-chlorophenylacetyl chloride (CPAC) to the surface of a dry PVA-H in tetrahydrofuran (THF)
Figure 25:
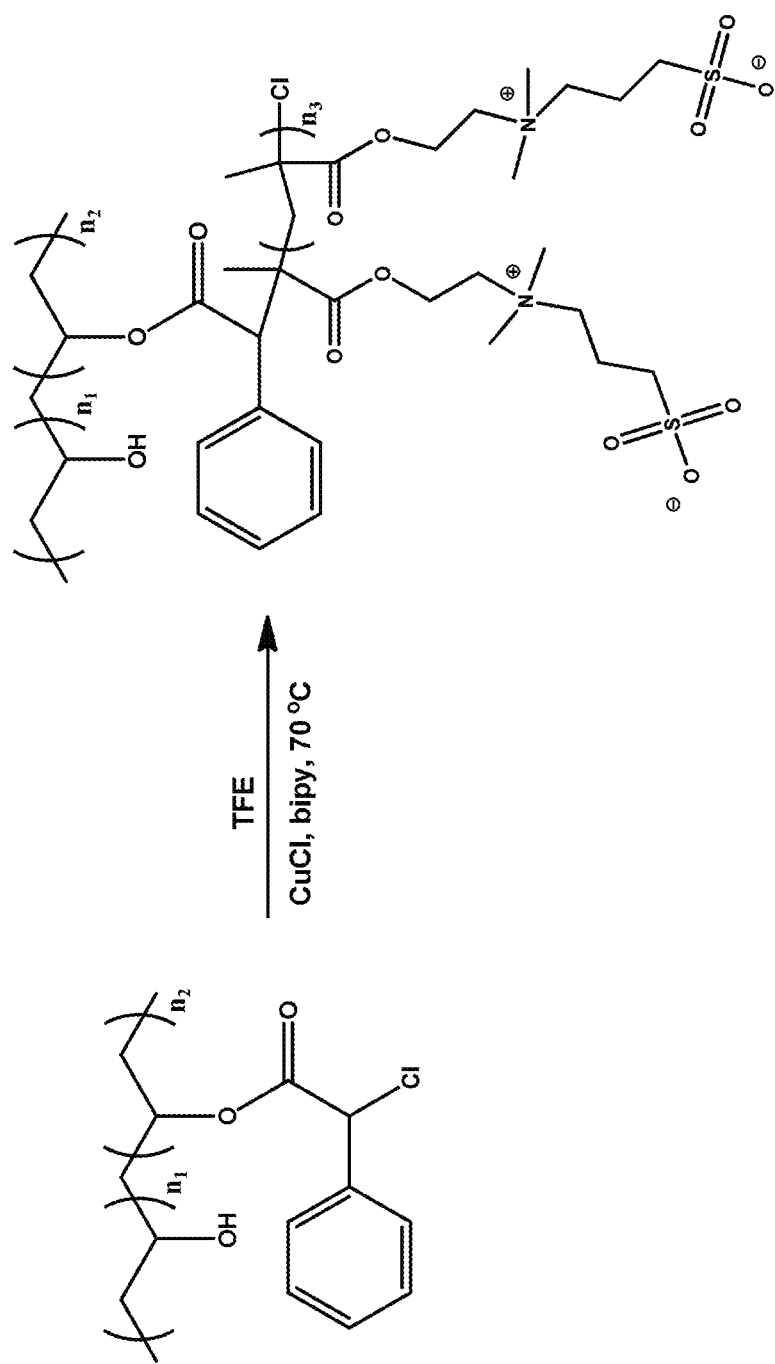
FIG. 25 is a schematic showing surface initiated polymerization of PMEDSAH from surface of the initiator functionalized hydrogel (CPAC-PVA) in triflureoethanol (TFE)
Figure 26:
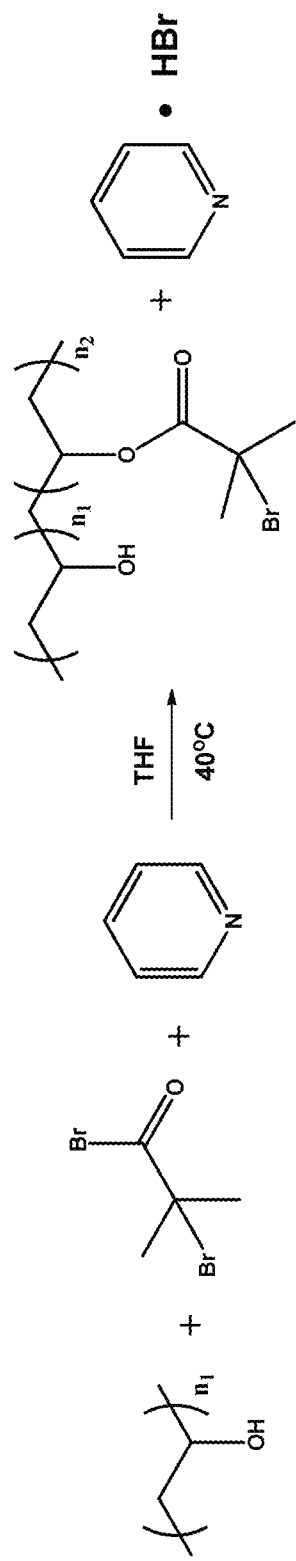
FIG. 26 is a schematic showing grafting of ATRP initiator α-bromoisobutyryl bromide (BB) to the surface of a dry PVA-H in THF.
Figure 27:
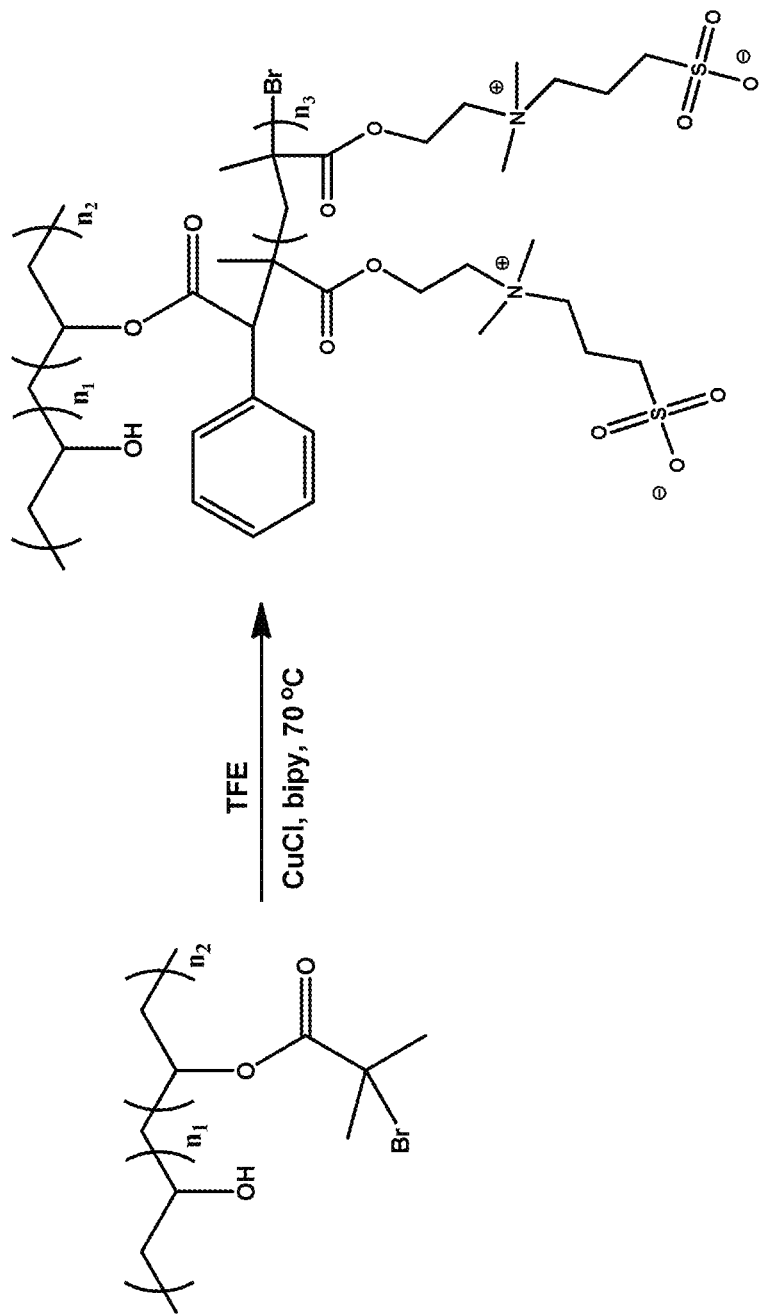
FIG. 27 is a schematic showing surface initiated polymerization of PMEDSAH from surface of the initiator functionalized hydrogel (BB-PVA) in TFE.

Referring to FIG. 24, one approach involves grafting of the ATRP initiator α-chlorophenylacetyl chloride (CPAC) to the surface of a dry PVA-H in tetrahydrofuran (THF). Next, surface initiated polymerization of PMEDSAH may be conducted from the surface of the initiator functionalized hydrogel (CPAC-PVA) in triflureoethanol (TFE), as seen in FIG. 25. Alternatively, as seen in FIG. 26, the ATRP initiator α-bromoisobutyryl bromide (BB) may be grated to the surface of a dry PVA-H in THF. Next, surface initiated polymerization of PMEDSAH may be performed from the surface of the initiator functionalized hydrogel (BB-PVA) in TFE, as seen in FIG. 27.

Figure 28:
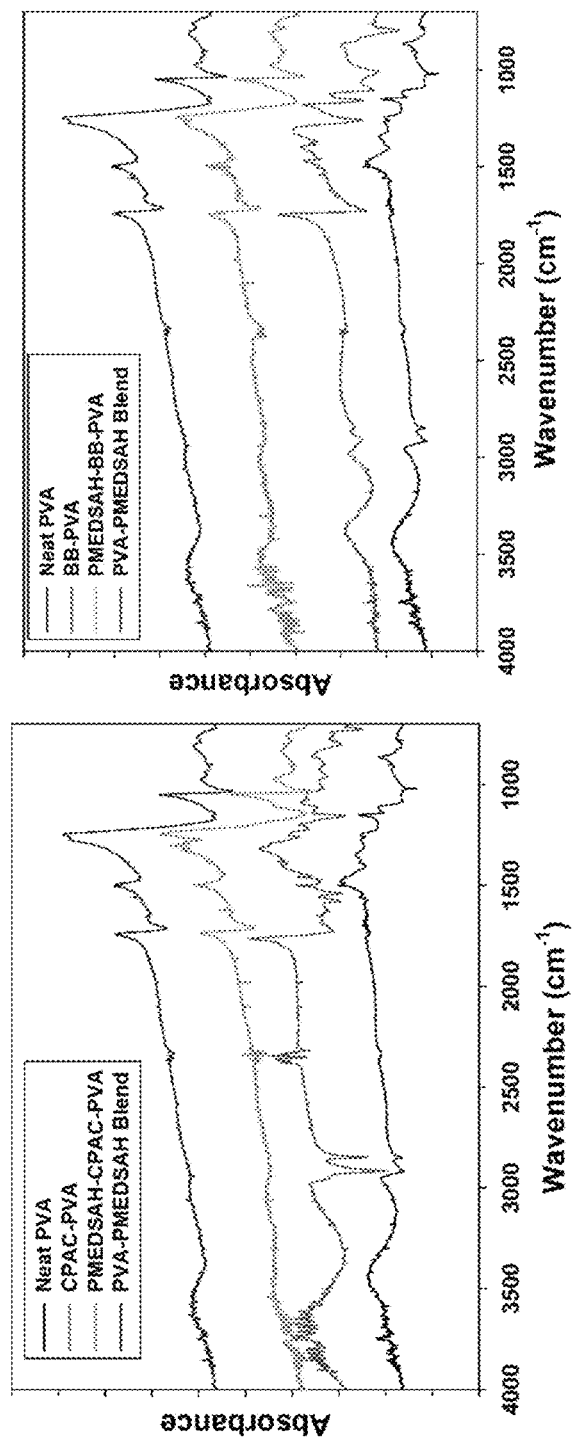
FIG. 28 are graphs of representative ATR-FTIR spectra of brush functionalized PVA-H initiated by CPAC (left) and BB (right).

Referring to FIG. 28, the success of both approaches was verified with attenuated total reflectance Fourier transform infrared spectroscopy (ATR-FTIR). As seen in Table 2 below, the measurement of coefficient of via the custom designed tribo-rheometry setup indicates that the PVA-PMEDSAH brush functionalized hydrogels display ionic responsive coefficient of friction.

TABLE 2

| COF in DI water | COF in 0.2M NaCl | COF in 0.5M NaCl |
|---|---|---|
| 0.49 ± 0.013 | 0.18 ± 0.0194 | 0.24 ± 0.0719 |

What is claimed is:

1. A hydrogel having self-replenishing lubrication, comprising:
   a matrix formed from a hydrogel polymer; and
   a plurality of sulfobetaine zwitterionic polymer molecules blended in the matrix.

2. The hydrogel of claim 1, wherein the hydrogel polymer comprises poly(vinyl alcohol).

3. A hydrogel having self-replenishing lubrication, comprising:
   a matrix formed from poly(vinyl alcohol);
   a plurality of zwitterionic polymer molecules blended in the matrix, wherein the zwitterionic polymer molecules comprise poly[2-(Methacryloyloxy) ethyl]dimethyl-(3-sulfopropyl) ammonium hydroxide).

4. The hydrogel of claim 3, wherein the hydrogel polymer comprises poly(vinyl alcohol) and an initiator grafted to a surface of the poly(vinyl alcohol).

5. The hydrogel of claim 4, wherein the initiator is α-chlorophenylacetyl chloride.

6. The hydrogel of claim 5, wherein the plurality of zwitterionic polymer molecules are polymerized from the α-chlorophenylacetyl chloride initiator.

7. The hydrogel of claim 4, wherein the initiator is α-bromoisobutyryl bromide.

8. The hydrogel of claim 5, wherein the plurality of zwitterionic polymer molecules are polymerized from the α-bromoisobutyryl bromide initiator.

9. The hydrogel of claim 1, wherein the hydrogel has an average modulus of above one Megapascal.

10. A method of making a hydrogel having self-replenishing lubrication, comprising the steps of:
    forming a plurality of zwitterionic polymer molecules comprising poly[2-(Methacryloyloxy) ethyl]dimethyl-(3-sulfopropyl) ammonium hydroxide);
    blending the plurality of zwitterionic polymer molecules with a hydrogel polymer comprising poly(vinyl alcohol);
    subjecting the blended zwitterionic polymer molecules and polymer to a predetermined number of freeze-thaw cycles to embed the zwitterionic polymer molecules in a matrix of the hydrogel polymer.

11. The hydrogel of claim 10, wherein the hydrogel has an average modulus of above one Megapascal.

12. A method of making a hydrogel having self-replenishing lubrication, comprising the steps of:
    grafting an initiator to a surface of a dry hydrogel polymer comprising poly(vinyl alcohol);
    initiating polymerization of plurality of zwitterionic molecules comprising poly[2-(Methacryloyloxy) ethyl]dimethyl-(3-sulfopropyl) ammonium hydroxide) from the initiator of the surface of the dry hydrogel polymer.

13. The method of claim 12, wherein the initiator comprises a-chlorophenylacetyl chloride.

14. The method of claim 13, wherein the initiator comprises α-bromoisobutyryl bromide.

15. The method of claim 12, wherein the step of grafting the initiator to the surface of the dry hydrogel is performed in the presence of tetrahydrofuran.

16. The method of claim 15, wherein the step of initiating polymerization of plurality of zwitterionic molecules from the initiator of the surface of the dry hydrogen polymer is performed in the presence of triflureoethanol.

* * * * *